US008680486B2

(12) United States Patent
Kimura

(10) Patent No.: US 8,680,486 B2
(45) Date of Patent: Mar. 25, 2014

(54) BIOLOGICAL MOLECULE DETECTING APPARATUS AND BIOLOGICAL MOLECULE DETECTING METHOD

(71) Applicant: Fujifilm Corporation, Tokyo (JP)

(72) Inventor: Toshihito Kimura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/854,640

(22) Filed: Apr. 1, 2013

(65) Prior Publication Data

US 2013/0224764 A1  Aug. 29, 2013

(30) Foreign Application Priority Data

Sep. 30, 2010 (JP) .................................. 2010-222999
Jun. 1, 2011 (JP) .................................. 2011-123101

(51) Int. Cl.
*G01N 21/64* (2006.01)

(52) U.S. Cl.
USPC ................... 250/461.2; 250/458.1; 250/459.1

(58) Field of Classification Search
USPC ........... 250/461.2, 458.1, 459.1, 338.1, 339.1
See application file for complete search history.

(56) References Cited

U.S. PATENT DOCUMENTS

| 5,811,312 | A | 9/1998 | Hasegawa et al. |
| 6,448,018 | B1 | 9/2002 | Nakayama et al. |
| 2004/0239854 | A1 | 12/2004 | Monobe |
| 2013/0217035 | A1* | 8/2013 | Kimura .......................... 435/7.4 |
| 2013/0224763 | A1* | 8/2013 | Kimura .......................... 435/7.4 |

FOREIGN PATENT DOCUMENTS

| JP | 61-272637 A | 12/1986 |
| JP | 62038346 A | 2/1987 |
| JP | 7-120397 A | 5/1995 |
| JP | 10-104079 A | 4/1998 |
| JP | 2000-19172 A | 1/2000 |
| JP | 2003-315258 A | 11/2003 |
| JP | 2008-298743 A | 12/2008 |
| WO | 03/024586 A1 | 3/2003 |

OTHER PUBLICATIONS

International Search Report of PCT/JP2011/005487, dated Dec. 27, 2011.
Written Opinion of the International Searching Authority dated Dec. 27, 2011 in corresponding International Patent Application No. PCT/JP2011/005487, 7 pages in Japanese and English.

* cited by examiner

*Primary Examiner* — David Porta
*Assistant Examiner* — Gisselle Gutierrez
(74) *Attorney, Agent, or Firm* — Sughrue Mion, PLLC

(57) ABSTRACT

A biological molecule detecting apparatus capable of highly sensitive measurements is provided. The emission direction of an orientation controlling light beam was periodically switched, to periodically switch the orientation direction of binding molecules 15 within a solution. Components, which are synchronized with the orientation periods of the binding molecules are extracted from fluorescence emitted by fluorescent molecules within the solution, are extracted and detected. Thereby, the concentration of a detection target substance can be accurately measured with a simple configuration.

19 Claims, 20 Drawing Sheets

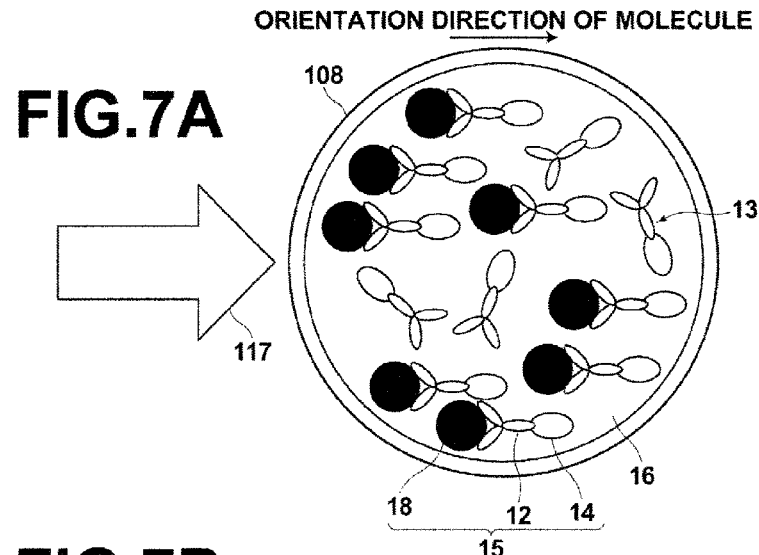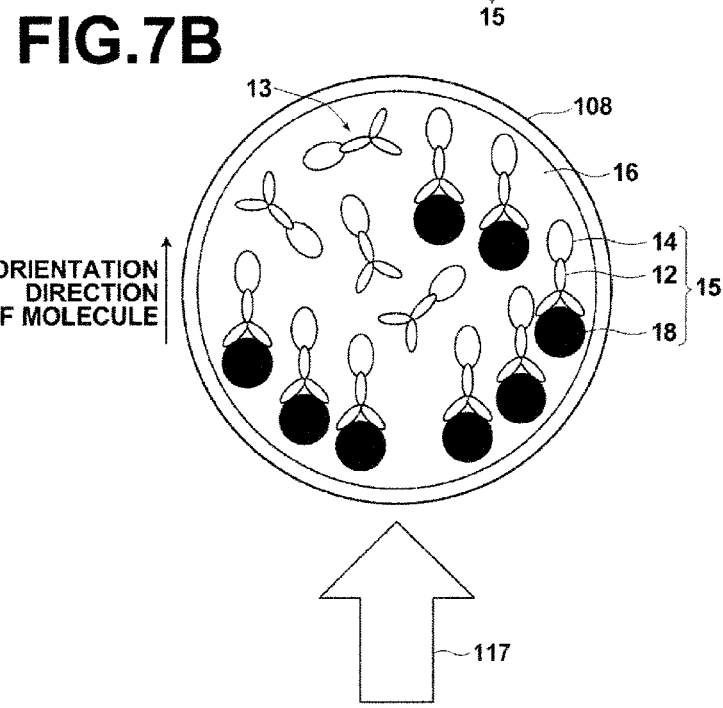

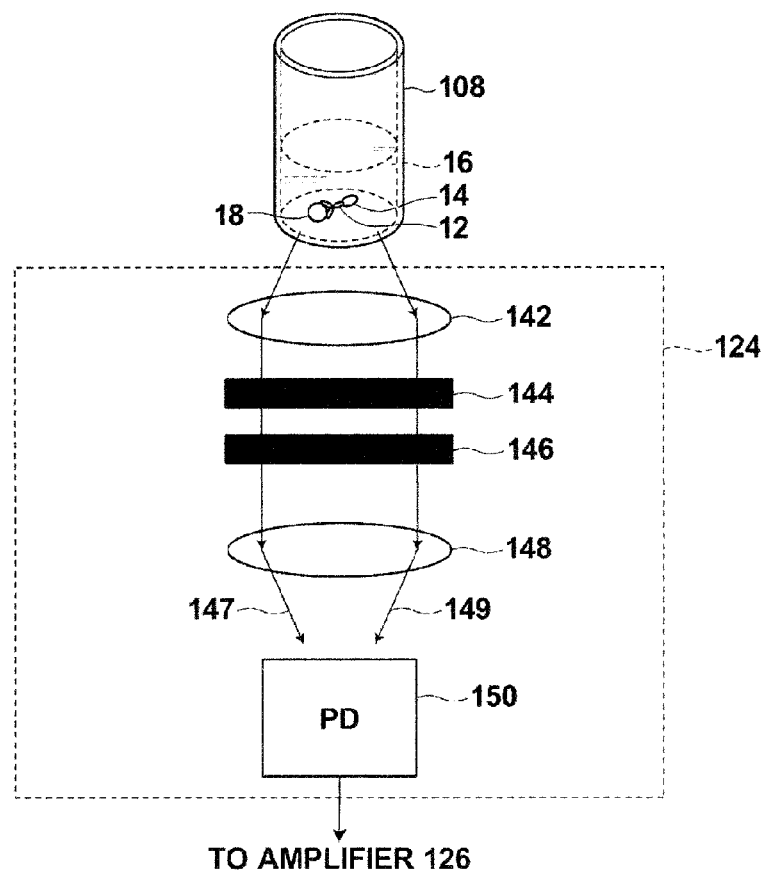

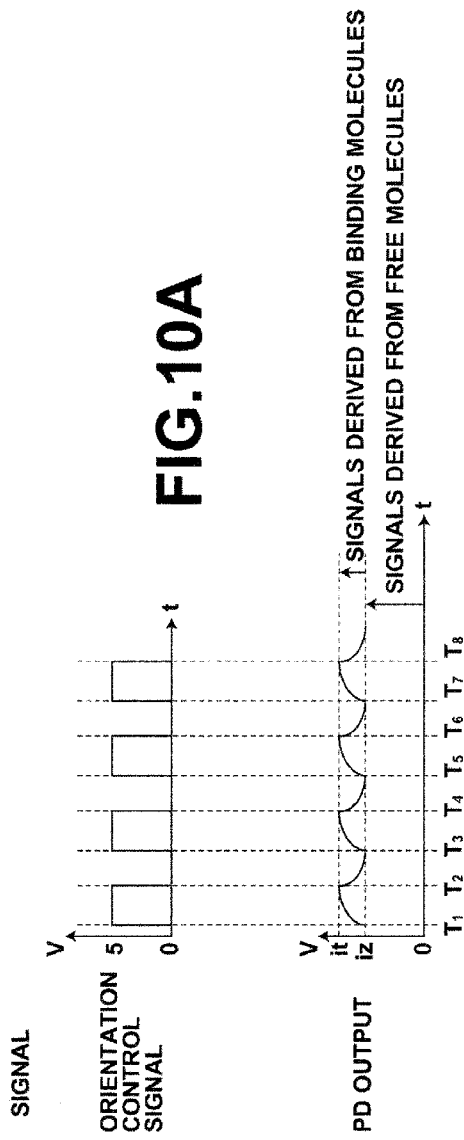
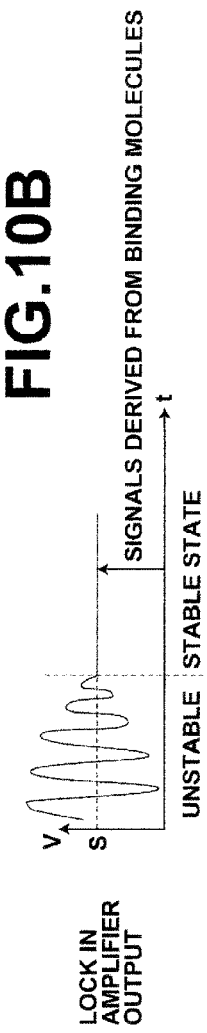
FIG.10A
FIG.10B

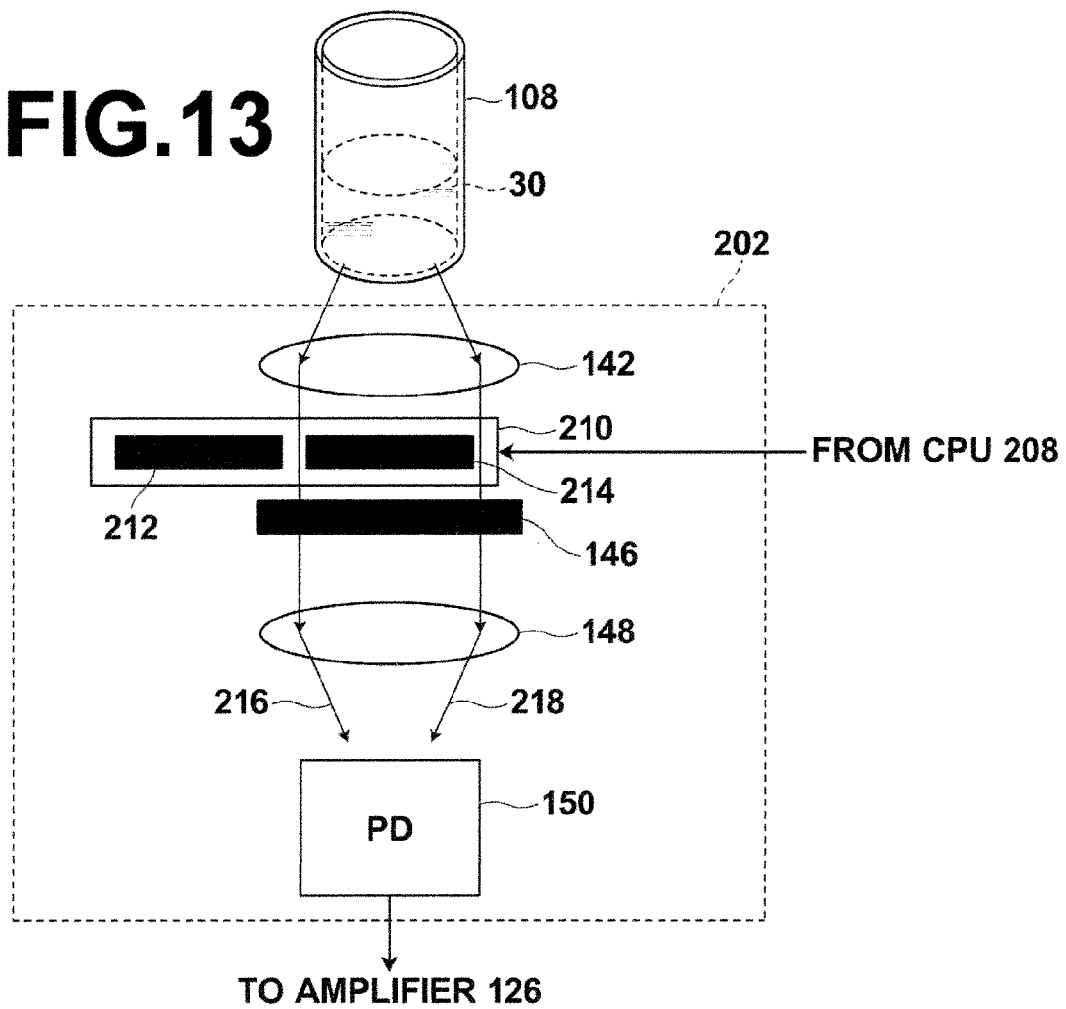

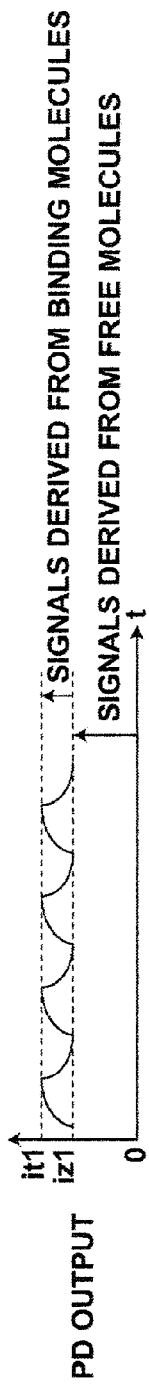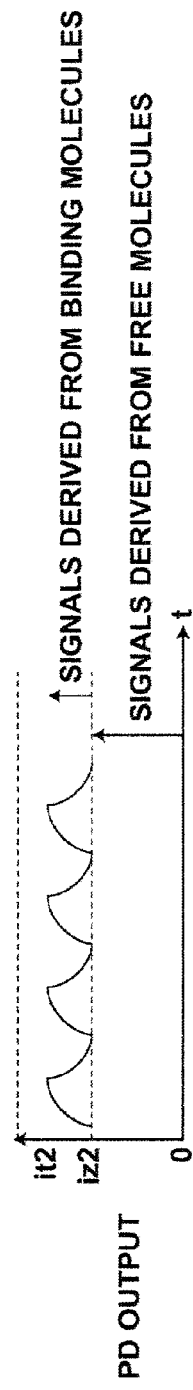

BIOLOGICAL MOLECULE DETECTING APPARATUS AND BIOLOGICAL MOLECULE DETECTING METHOD

TECHNICAL FIELD

The present invention is related to technology for detecting detection target substances within solutions. Particularly, the present invention is related to a biological molecule detecting apparatus and a biological molecule detecting method capable of detecting biological molecules, viruses, nucleic acids, proteins, and germs within samples.

BACKGROUND ART

Recently, biological molecule detecting methods, in which physicians or technicians detect biological molecules at points of care, immediately obtain measurement results, and utilize the measurement results for diagnosis and treatment, are being focused on. Biological molecule detecting methods are methods for selectively detecting only detection target substances from within bodily fluids such as blood, urine, and sweat, by the high selectivity of specific reactions such as antigen antibody reactions. Such biological molecule detecting methods are particularly widely employed to detect, inspect, quantify, and analyze small amounts of biological molecules, such as viruses, nucleic acids, proteins, and germs.

Radioimmunoassay is a biological molecule detecting method which is in practical use. Radioimmunoassay employs antigens or antibodies labeled with isotopes, and detects the presence of antibodies or antigens that specifically bind with the labeled antigens or the labeled antibodies.

Fluorescence immunoassay is a biological molecule detecting method that does not employ radioactive substances. Fluorescence immunoassay apparatuses, in which antibodies are immobilized onto a reaction layer in advance (referred to as a solid phase), a measurement target solution and antibodies labeled with fluorescent molecules are caused to flow onto the reaction layer, and fluorescence in the vicinity of the reaction layer is observed to measure the concentration of antigens which have specifically bound to the antibodies, are known (refer to Japanese Unexamined Patent Publication No. 7 (1995)-120397, for example).

However, fluorescence immunoassay that utilizes solid phases has a problem that it is costly to produce the solid phases. There is a method that utilizes fluorescence polarization method to confirm antigen antibody reactions in solutions (referred to as a liquid phase) as a method that does not employ solid phases. The fluorescence polarization method is a method that detects changes in degrees of fluorescence polarization caused by changes in Brownian motion that occurs by the sizes of molecules changing by molecules binding with molecules which have fluorescent labels. The biological molecule detecting method that utilizes the fluorescence polarization method is known as a simple and expedient method for detecting detection target substances within samples (refer to Japanese Unexamined Patent Publication No. 2008-298743, for example).

DISCLOSURE OF THE INVENTION

However, the conventional fluorescence polarization method utilizes changes in Brownian motion, which is random, and therefore has a problem that there is a limit to measurement sensitivity. In addition, the method disclosed in Japanese Unexamined Patent Publication No. 2008-298743 requires that fluorescent lifetimes are long enough to be influenced by changes in Brownian motion. However, fluorescence lifetimes are influenced by components within samples. Therefore, there are cases in which fluctuations will occur in the measurement results obtained by the method of Japanese Unexamined Patent Publication No. 2008-298743.

The present invention has been developed in view of the foregoing circumstances. It is an object of the present invention to provide a biological molecule detecting apparatus and a biological molecule detecting method, which are capable of highly sensitive measurements.

A biological molecule detecting apparatus of the present invention that achieves the above object is that which detects fluorescence emitted by a first complex and a second complex within a solution, the first complex being formed by a substance that specifically binds with a detection target substance bound to a fluorescent molecule, and the second complex being formed by the first complex bound to the detection target substance, to detect or quantify the detection target substance, comprising:

a light source that emits excitation light having a light component which is linearly polarized in a specific direction that excites the fluorescent molecules;

a light receiving section that detects the fluorescence emitted by the fluorescent molecules;

orientation control means for periodically switching the orientation of the second complex within the solution;

synchronous component extracting means for extracting components of the fluorescence detected by the light receiving section which are synchronized with the period at which the second complex is oriented; and a calculating section that detects or quantifies the detection target substance based on the component extracted by the synchronous component extracting means.

It is preferable for the biological molecule detecting apparatus of the present invention to adopt a configuration, wherein:

the orientation control means switches the orientation of the second complex between an orientation in a first direction in which the direction of the transition moments and the vibration direction of the linearly polarized component of the excitation light are parallel, and an orientation in a second direction in which the direction of the transition moments and the vibration direction are perpendicular.

It is preferable for the biological molecule detecting apparatus of the present invention to adopt a configuration, wherein:

the period at which the orientation of the second complex is switched is determined by one of the molecular weight and the volume of the detection target substance, one of the molecular weight and the volume of the substance that specifically binds to the detection target substance, one of the molecular weight and the volume of the fluorescent molecule, and the intensity of orientation control exerted by the orientation control means.

It is preferable for the biological molecule detecting apparatus of the present invention to adopt a configuration, wherein:

the orientation control means is equipped with an orientation controlling light source that emits light having a wavelength different from that of the excitation light, that controls the orientation of the second complex. In this case, it is preferable for the orientation controlling light source to emit the light having a wavelength different from that of the excitation light onto the solution from a plurality of positions.

It is preferable for the biological molecule detecting apparatus of the present invention to further comprise:

a solution holding portion for holding the solution, having a flat surface at least at a portion thereof. In this case, it is preferable for the orientation controlling light source to emit the light having a wavelength different from that of the excitation light in a direction that passes through the solution and exits the flat surface of the solution holding portion such that the light is focused at an interface between the solution and the flat surface.

It is preferable for the biological molecule detecting apparatus of the present invention to adopt a configuration, wherein:

the light receiving section is equipped with spectral means for spectrally separating light. In this case, it is preferable for the spectral means to be a plurality of filters having different properties; and for the light receiving section to switch a filter to be employed from among the plurality of filters according to the emission wavelength of the fluorescence.

A biological molecule detecting method of the present invention is that which detects fluorescence emitted by a first complex and a second complex within a solution, the first complex being formed by a substance that specifically binds with a detection target substance bound to a fluorescent molecule, and the second complex being formed by the first complex bound to the detection target substance, to detect or quantify the detection target substance, comprising:

a step of emitting excitation light having a light component which is linearly polarized in a specific direction that excites the fluorescent molecules;

a step of periodically switching the orientation of the second complex within the solution;

a step of detecting the fluorescence emitted by the fluorescent molecules;

a step of extracting components of the detected fluorescence which are synchronized with the period at which the second complex is oriented; and a step of detecting or quantifying the detection target substance based on the extracted component.

The present invention enables highly sensitive detection of biological molecules.

BRIEF DESCRIPTION OF THE DRAWINGS

FIG. 7A is a schematic diagram that illustrates the relationship between a first orientation controlling light beam emission direction and the orientation direction of a binding molecule.

FIG. 7B is a schematic diagram that illustrates the relationship between an emission direction of the second orientation controlling light beam perpendicular to the emission direction illustrated in FIG. 7A and the orientation direction of a binding molecule.

FIG. 8 is a schematic diagram that illustrates the detailed structure of a light receiving section of the biological molecule detecting apparatus according to the first embodiment.

FIG. 10A is a graph that illustrates orientation control signals and PD output in the biological molecule detecting apparatus according to the first embodiment.

FIG. 10B is a graph that illustrates lock in amplifier output in the biological molecule detecting apparatus according to the first embodiment.

FIG. 13 is a schematic diagram that illustrates the detailed structure of a light receiving section of the biological molecule detecting apparatus according to the second embodiment.

FIG. 14A is a graph that illustrates PD output with respect to a first detection target substance in the second embodiment.

FIG. 14B is a graph that illustrates PD output with respect to a second detection target substance in the second embodiment.

BEST MODE FOR CARRYING OUT THE INVENTION

Hereinafter, embodiments of the present invention will be described with reference to the attached drawings. Various specific reactions are utilized to detect biological molecules. Here, apparatuses that utilize specific reactions between antigens and antibodies, and detect antigens which have reacted with the antibodies, based on fluorescence emitted by fluorescent molecules which are bound to the antibodies as labels, will be described as examples.

First Embodiment

Figure 1A:
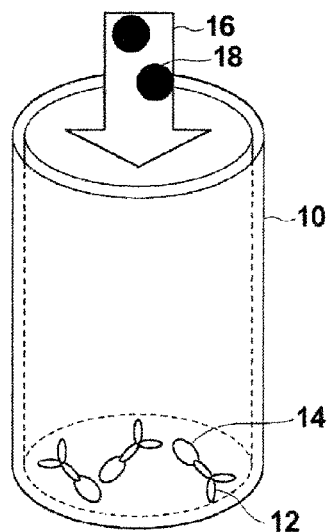
FIG. 1A is a first schematic diagram that illustrates antigen antibody reactions in a biological molecule detecting apparatus according to a first embodiment.
Figure 1B:
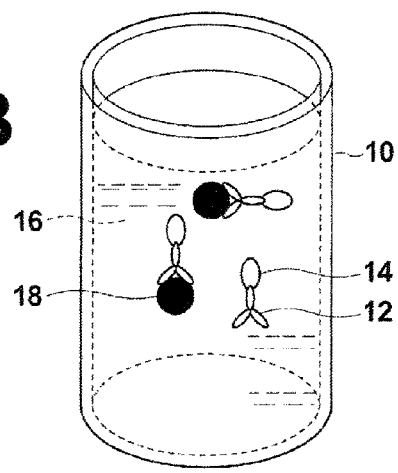
FIG. 1B is a second schematic diagram that illustrates antigen antibody reactions in the biological molecule detecting apparatus according to the first embodiment.

FIG. 1A and FIG. 1B are schematic diagrams that illustrate antigen antibody reactions in a biological molecule detecting apparatus according to a first embodiment. Antigen antibody reactions within a liquid will be described with reference to FIG. 1A and FIG. 1B. Here, a case will be considered in which dry antibodies 12 are placed in a cylindrical reagent cup 10. The antibodies 12 are labeled with fluorescent molecules 14.

In the present embodiment, plasma 16 separated from whole blood is employed as a sample. The plasma 16 is dispensed into the reagent cup 10 and stirred. In the case that antigens 18 that specifically bind with the antibodies 12 are present in the plasma 16, antigen antibody reactions will occur between the antibodies 12 and the antigens 18, and the antibodies 12 and the antigens 18 will be present within the plasma 16 in a specifically bound state, as illustrated in FIG. 1B.

In the present embodiment, a case will be described in which the plasma 16 separated from whole blood is employed as the sample, PSA (Prostate Specific Antigens) are the antigens 18 as the detection target substance, and anti PSA antibodies are employed as the antibodies 12 that specifically bind with the detection target substance. Alexa Fluor 568 (by Molecular Probes) is employed as the fluorescent molecules 14. Alexa Fluor 568 emits fluorescence having wavelengths within a range from 550 nm to 700 nm, with a peak at approximately 610 nm.

A sufficiently great amount of the antibodies 12 is supplied with respect to the antigens 18. Therefore, a portion of the antibodies 12 remain within the plasma 16 without undergoing antigen antibody reactions. Hereinafter, the antibodies 12, the antigens 18, and the fluorescent molecules 14 which are bound to each other by antigen antibody reactions will be referred to as binding molecules, and the antigens 12 and the fluorescent molecules 14 which have not undergone antigen antibody reactions but are present in the liquid will be referred to as free molecules. The binding molecules and the free molecules are both present in the plasma 16. Note that components other than the antigens 18 are present in the plasma 16. However, components other than the antigens 18 are omitted from FIG. 1A and FIG. 1B in order to simplify the description.

The biological molecule detecting apparatus according to the first embodiment of the present invention emits excitation light into the solution, in which the binding molecules and the free molecules are both present, as the solution is a liquid phase. Fluorescence emitted by the fluorescent molecules 14 is received, and detection and quantification of the antigens 18 is performed based on the received fluorescence. Accordingly, it is desirable for only fluorescence emitted from the binding molecules that include the antigens 18 to be detected. However, the free molecules and the binding molecules are both present in the solution. Therefore, when the excitation light is emitted into the solution, the fluorescent molecules 14 associated with the free molecules also emit fluorescence, resulting in unnecessary fluorescent components being generated. Therefore, the biological molecule detecting apparatus according to the first embodiment of the present invention calculates the fluorescence contributed by fluorescent molecules associated with free molecules from among the entirety of fluorescence data.

Excitation efficiency of the fluorescent molecules 14 by linearly polarized excitation light will be described with reference to FIGS. 2A and 2B in order to explain the principle of calculating the fluorescence contributed by the binding molecules and the fluorescence contributed by the free molecules in the biological molecule detecting apparatus 100 according to the first embodiment.

Figure 2A:
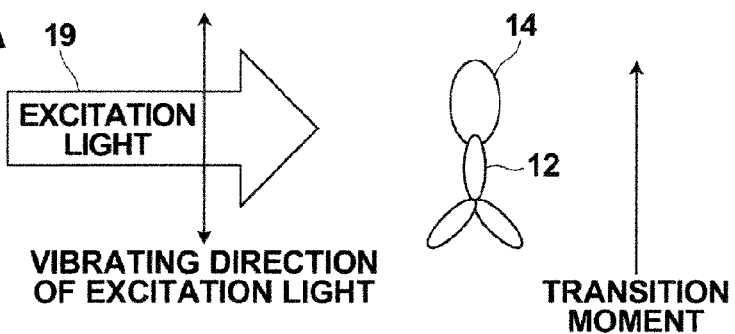
FIG. 2A is a schematic diagram that illustrates a case in which the vibration direction of excitation light and the transition moment of a fluorescent molecule are parallel.
Figure 2B:
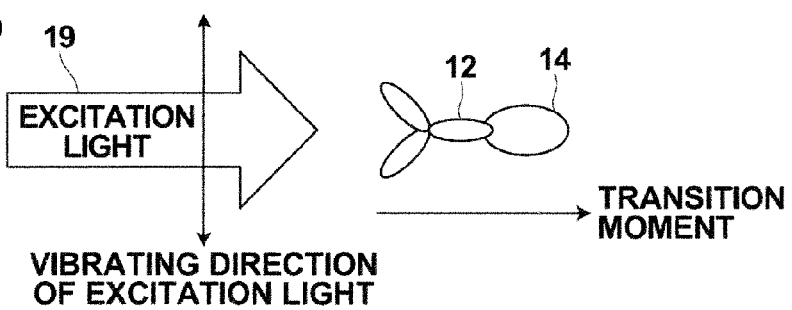
FIG. 2B is a schematic diagram that illustrates a case in which the vibration direction of excitation light and the transition moment of a fluorescent molecule are perpendicular.

FIG. 2A is a schematic diagram that illustrates a case in which the vibration direction of excitation light 19 and the transition moment of a fluorescent molecule 14 are parallel. FIG. 2B is a schematic diagram that illustrates a case in which the vibration direction of excitation light 19 and the transition moment of a fluorescent molecule 14 are perpendicular. Here, cases are described in which the longitudinal direction of the fluorescent molecule 14 is parallel to the orientation direction of the transition moment, to simplify the description. Note that in the present specification, the "vibration direction" of light refers to the vibration direction of an electric field. In the case that light is polarized, the vibration direction is the same as the polarization direction.

The fluorescent molecules 14 transition to an excited state when light energy is absorbed, and emits fluorescence during the process of returning to a baseline state. The fluorescent molecules 14 transition to an excited state when light energy is absorbed, and emits fluorescence during the process of returning to a baseline state. When a fluorescent molecule 14 is excited by linearly polarized excitation light 19, the fluorescent molecule 14 emits fluorescence which is polarized in the same direction as the polarization direction of the excitation light. The degree of polarization of fluorescence emitted by the fluorescent molecules 14 depends on the speed of rotational movement thereof. That is, if a fluorescent molecule 14 is not undergoing rotational movement, the fluorescent molecule 14 emits fluorescence which is polarized in the same direction as the vibration direction of the excitation light 19. The degree of polarization of the fluorescence emitted by fluorescent molecules 14 decreases as the speed at which they are undergoing rotational movement becomes greater.

When the fluorescent molecules 14 are excited, vectors within the fluorescent molecules called transition moments, which are determined by the molecular structures of the fluorescent molecules 14, interact with the excitation light 19. The transition moments have unique directions within the fluorescent molecules 14, and the relationship between the directions of the transition moments and the vibration direction of the excitation light 19 determines the excitation efficiency of the fluorescent molecules 14. Specifically, the fluorescent molecules 14 selectively absorb light that vibrates in a direction parallel to the transition moments thereof. Accordingly, in the case that the excitation light 19 is emitted onto a fluorescent molecule 14 while vibrating in the vertical direction of the drawing sheet and propagating from the left to the right of the drawing sheet as illustrated in FIGS. 2A and 2B, the excitation efficiency becomes greatest in the case that the vibration direction of the excitation light 19 is parallel to the transition moment of the fluorescent molecule 14 (FIG. 2A), and becomes 0 in the case that the vibration direction of the excitation light 19 is perpendicular to the transition moment of the fluorescent molecule 14 (FIG. 2B). The orientations of the transition moments change according to the orientations of the fluorescent molecules 14, and therefore the orientations of the fluorescent molecules 14 within the solution influence the excitation efficiencies thereof.

Figure 3A:
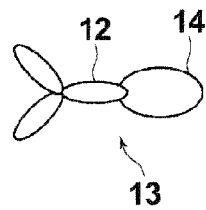
FIG. 3A is a schematic diagram that illustrates a free molecule (an antibody and a fluorescent molecule to which an antigen is not bound).
Figure 3B:
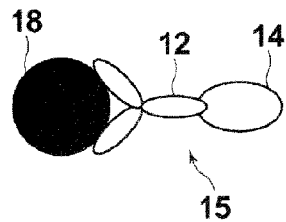
FIG. 3B is a schematic diagram that illustrates a binding molecule (an antibody and a fluorescent molecule to which an antigen is bound).

Motion of the free molecules and the binding molecules within the solution will be described with reference to FIGS. 3A and 3B in order to consider the orientations of the fluorescent molecules 14 within the solution. FIG. 3A is a schematic diagram that illustrates an antibody 12 and a fluorescent molecule 14, the combination of which is a free molecule. FIG. 3B is a schematic diagram that illustrates an antibody 12, an antigen 18, and a fluorescent molecule 14, the combination of which is a binding molecule.

The free molecules and the binding molecules move irregularly (Brownian motion) within the solution, and undergo movement within the solution and rotational movement. It is known that Brownian motion of molecules within solutions is influenced by absolute temperature, the volumes of the molecules, the molecular weights (mass) of the molecules, the viscosity of the solutions, etc. The volumes of the binding molecules are greater than those of the free molecules due to the antigens 18 being bound thereto, and are less likely to undergo Brownian motion within the solution. A technique that utilizes the difference in Brownian motion of free molecules 13 and binding molecules 15 within solutions to detect binding molecules 15 from changes in Brownian motion is known. However, because Brownian motion is random, detection sensitivity is limited.

The biological molecule detecting apparatus according to the first embodiment of the present invention utilizes laser beams to periodically orient the binding molecules 15 within the solution, and detects only signals corresponding to the orientation period, to calculate the contribution of fluorescence emitted by the binding molecules 15.

When a laser beam is emitted onto the free molecules 13 and the binding molecules 15 within the solution, external force is imparted onto the free molecules 13 and the binding molecules 15, and Brownian motion thereof is inhibited. If the external force imparted onto the binding molecules 15 by the laser beam is designated as Fb and the external force imparted onto the free molecules by the laser beam is designated as Ff, the intensity of the external force which is imparted onto the free molecules 13 and the binding molecules 15 differ because the volumes and the masses differ according to the presence or absence of the antigens 18, and Fb>Ff.

In addition, the ease with which the free molecules 13 and the binding molecules 15 undergo Brownian motion within the solution differs due to the differences in the volumes and molecular weights thereof. The free molecules 13 have smaller volumes and molecular weights than the binding molecules 15, and therefore undergo Brownian motion with greater ease. If the force necessary to orient the binding molecules 15 is designated as Bb, and the force necessary to orient the free molecules 13 is designated as Bf, Bb>Bf. If Fb>Bb, then the binding molecules 15 will be oriented, and if Ff<Bf, the free molecules 13 will not be oriented.

The biological molecule detecting apparatus according to the first embodiment of the present invention periodically orients only the binding molecules 15, and calculates the contribution of fluorescence emitted by the binding molecules 15 by detecting only signals that correspond to the orientation period. Factors such as the absolute temperature of the solution, the volumes of molecules, the molecular weights of the molecules, the viscosity of a solvent, and the intensity of a laser are determined such that the binding molecules 15 will be oriented while the free molecules 13 will not, that is, such that Fb>Bb and Ff<Bf. The volumes and molecular weights of the molecules are often determined by the detection target substance, and the viscosity of the solution is often determined by the sample. Therefore, the biological molecule detecting apparatus according to the first embodiment of the present invention performs adjustments by changing the absolute temperature of the solution and the intensity of the laser beam such that conditions in which only the binding molecules 15 are oriented are achieved. For this reason, the biological molecule detecting apparatus according to the first embodiment of the present invention has the functions of adjusting the temperature of the solution and adjusting the intensity of the laser beam.

Figure 4A:
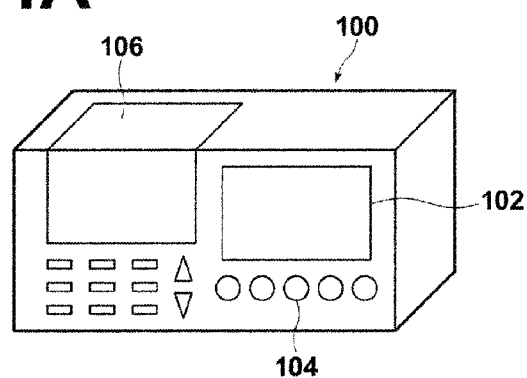
FIG. 4A is a perspective view that illustrates the outer appearance of the biological molecule detecting apparatus according to the first embodiment.

The configuration of the biological molecule detecting apparatus 100 according to the first embodiment of the present invention will be described. FIG. 4A is a perspective view that illustrates the outer appearance of the biological molecule detecting apparatus 100. A display section 102, a user input section 104, and an openable portion 106 are provided on a side surface of the biological molecule detecting apparatus 100. The display section 102 displays measurement results and the like. The user input section 104 is a section at which modes are set, sample data are input, etc. The openable portion 106 is of a configuration in which an upper lid may be opened. The upper lid is opened when samples are set, and closed during measurements. By adopting this configuration, light from the exterior influencing measurements can be prevented.

Figure 4B:
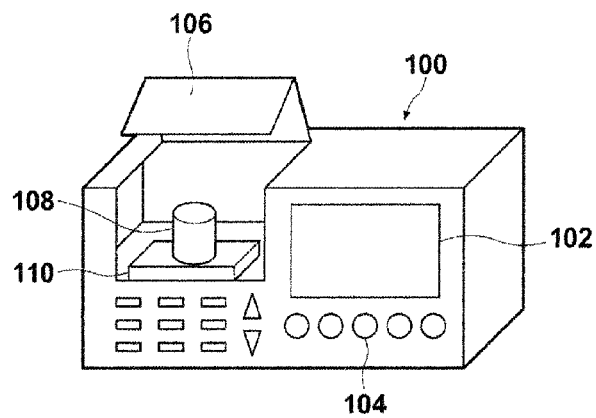
FIG. 4B is a diagram that illustrates the biological molecule detecting apparatus according to the first embodiment in a state in which an openable portion is opened.

FIG. 4B is a perspective view that illustrates the biological molecule detecting apparatus 100 in a state in which the openable portion 106 is opened. When the openable portion 106 is opened, a reagent cup 108 and a holding base 110 are present within the biological molecule detecting apparatus 100. The reagent cup 108 is removably held by the holding base 110. The reagent cup 108 is a cylindrical container in which solutions are placed. Users dispense samples into the reagent cup 108 and close the upper lid to perform measurements. Although not illustrated in the drawings, the biological molecule detecting apparatus 100 is also equipped with a reagent tank and a dispensing section. When measurements are initiated, the dispensing section suctions a reagent from within the reagent tank, and dispenses the reagent into the reagent cup 108.

Figure 5:
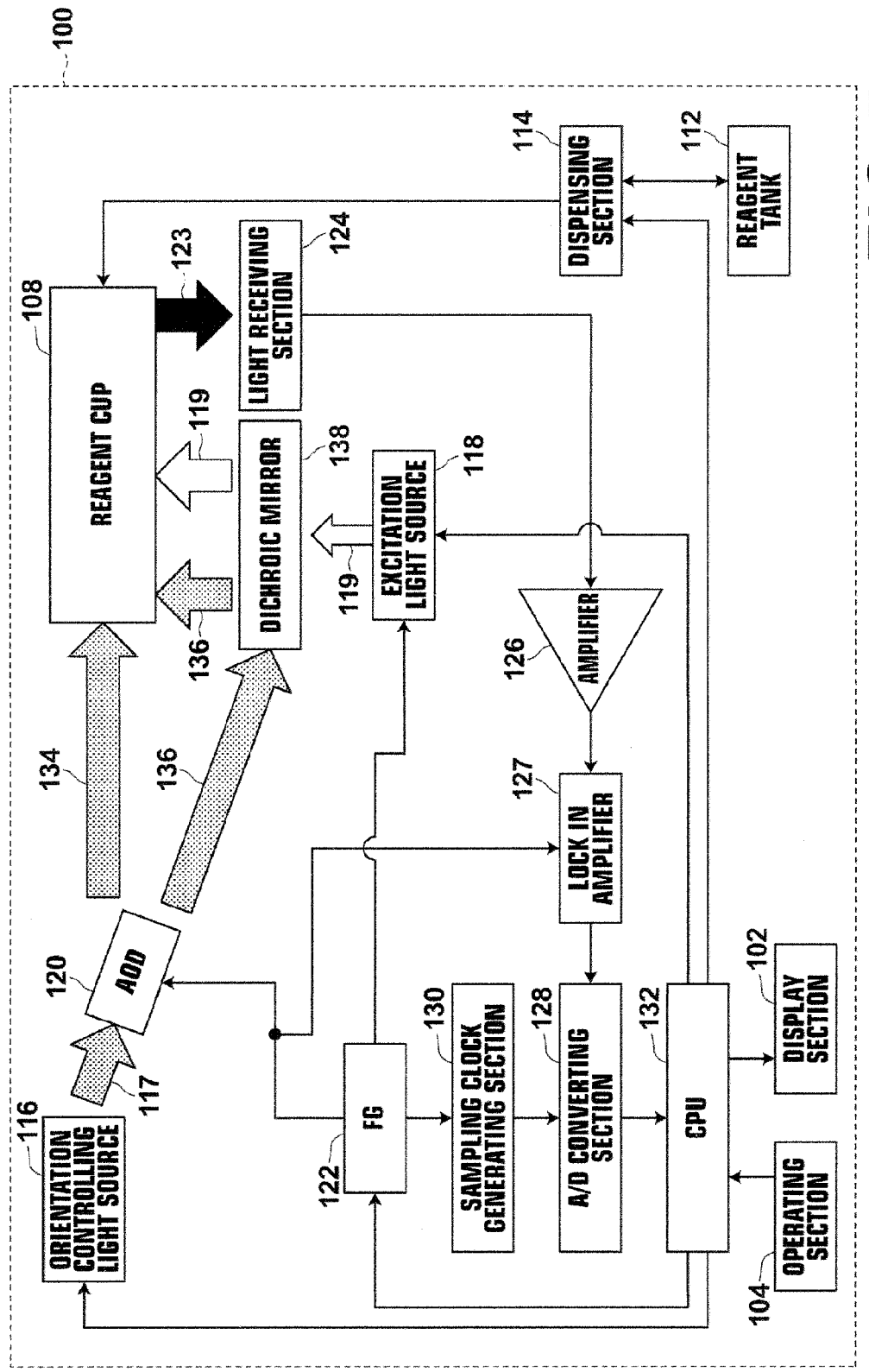
FIG. 5 is a block diagram that illustrates the main components of the biological molecule detecting apparatus.

FIG. 5 is a functional block diagram that illustrates the main components of the biological molecule detecting apparatus 100. The biological molecule detecting apparatus 100 includes: the display section 102, the user input section 104, the reagent cup 108, the reagent tank 112, the dispensing section 114, an orientation controlling light source 116, an excitation light source 118, an AOD (Acousto Optic Deflector) 120, a FG (Function Generator) 122, a light receiving section 124, an amplifier 126, a lock in amplifier 127, an A/D converting section 128, a sampling clock generating section 130, a CPU 132, and a dichroic mirror 138.

The reagent cup 108 is a container in which reagents stored in the reagent tank 112 and samples collected from patients or the like are caused to react. The reagent cup 108 is removably attached to the biological molecule detecting apparatus 100. The capacity of the reagent cup 108 is approximately 120 µL.

The reagent tank 112 is a tank in which a plurality of types of reagents are stored. The free molecules 13 are stored in the reagent tank 112 as reagents.

The dispensing section 114 is constituted by a removably pipette, a suctioning device, etc. The dispensing section 114 suctions reagents to be utilized for measurement from the reagent tank 112 and dispenses the suctioned reagents to the reagent cup 108, according to commands from the CPU 132.

The orientation controlling light source 116 emits an orientation controlling light beam 117 toward the AOD 120, and orients the binding molecules which are present in the solution within the reagent cup 108, by applying external force to the binding molecules. In the present specification, the orientation controlling light source 116 corresponds to the orientation controlling means of the present invention. A laser beam having a wavelength of 980 nm and an output of 700 mW, for example, is employed as the orientation controlling light beam 117. The orientation controlling light beam 117 is a laser beam that the fluorescent molecules 14 do not absorb, and is of an intensity that will not influence or destroy the dye of the fluorescent molecules 14. The orientation controlling light beam 117 has a width capable of illuminating the entirety of the solution within the reagent cup 108.

The excitation light source 118 emits excitation light 119, which is linearly polarized by a polarizing element provided within the excitation light source 118, that excites the fluorescent molecules 14, toward the reagent cup 108 via the dichroic mirror 138. Light having a wavelength of 532 nm and an output of 10 mW, for example, is employed as the excitation light.

The dichroic mirror 138 reflects light having a specific wavelength, and transmits light having other wavelengths. The dichroic mirror 138 reflects the orientation controlling light beam 117 and transmits the excitation light 119.

The AOD 120 utilizes the acoustic optical effect to change the refractive index of the interior thereof based on input voltages, to switch the direction in which light input thereto propagates. The AOD 120 changes the refractive index of the interior thereof to change the direction in which the orientation controlling light beam 117 propagates, based on voltages input according to voltage signals (hereinafter, the signals output to the AOD 120 will be referred to as "orientation control signals") output from the FG (Function Generator) 122. In other words, the direction in which the orientation controlling light beam 117 propagates is determined by the orientation control signals generated by the FG 122. The AOD 120 switches the direction in which the orientation controlling light beam 117 propagates between a direction that irradiates the reagent cup 108 (indicated by arrow 134 in FIG. 5) and a direction that irradiates the dichroic mirror 138 (indicated by arrow 136 in FIG. 5).

The FG 122 is a device capable of generating voltage signals having various frequencies and waveforms. The FG 122 outputs different voltage signals to the AOD 120, the lock in amplifier 127, and the sampling clock generating section 130 in response to commands received from the CPU 132.

The CPU 132 specifies orientation control signals to be output by the FG 122, and controls the timings at which the AOD 120 switches the directions in which the orientation controlling light beam 117 propagates.

The light receiving section 124 is constituted by filters, photodiodes, etc. The light receiving section 124 is provided beneath the reagent cup 108. The light receiving section 124 receives fluorescence 123 generated by the fluorescent molecules 14 within the reagent cup 108 under the reagent cup 108, converts the received fluorescence signals to analog electrical signals (analog fluorescence data), and outputs the analog electrical signals to the amplifier 126.

The amplifier 126 amplifies the analog fluorescence data output thereto from the light receiving section 124, and outputs the amplified analog fluorescence data to the lock in amplifier 127.

The lock in amplifier 127 converts the analog fluorescence data to direct current frequencies. Square waves are input to the lock in amplifier 127 from the FG 122 as a reference signal. The square waves have the same period as the voltage signals output from the FG 122 to the orientation controlling light source 116. The lock in amplifier 127 detects frequency components equal to the reference signal from among the analog fluorescence data output from the amplifier 126. Specifically, the lock in amplifier 127 converts only frequency components equal to the reference signal to direct current signals by synchronous detection, and transmits only the direct current signals through a low pass filter provided therein. The lock in amplifier 127 outputs the direct current signals to the A/D converting section 128. In the present specification, the lock in amplifier 127 corresponds to the synchronous component extracting means of the present invention.

The sampling clock generating section 130 inputs a sampling clock that specifies the timings at which the A/D converting section 128 is to sample the analog fluorescence data to the A/D converting section, based on voltage signals output thereto from the FG 122.

The A/D converting section 128 samples the analog fluorescence data output thereto from the amplifier 126, based on the sampling clock output thereto from the sampling clock generating section 130. The A/D converting section 128 converts the sampled analog fluorescence data to digital data, and outputs the digital data to the CPU 132.

The CPU 132 performs calculations using the digital data output thereto from the A/D converting section 128, and outputs the results of calculations to the display section 102. In addition, the CPU 132 controls the operations of the orientation controlling light source 116, the excitation light source 118, the dispensing section 114, and the FG 122 in response to commands input from the user input section 104. Specifically, the CPU 132 outputs ON/OFF commands to the orientation controlling light source 116 and the excitation light source 118, outputs commands that specify a reagent to be utilized and commands to initiate dispensing operations to the dispensing section 114, and outputs commands that specify the waveform of voltage signals to be output and commands to output the voltage signals to the FG 122.

Figure 6:
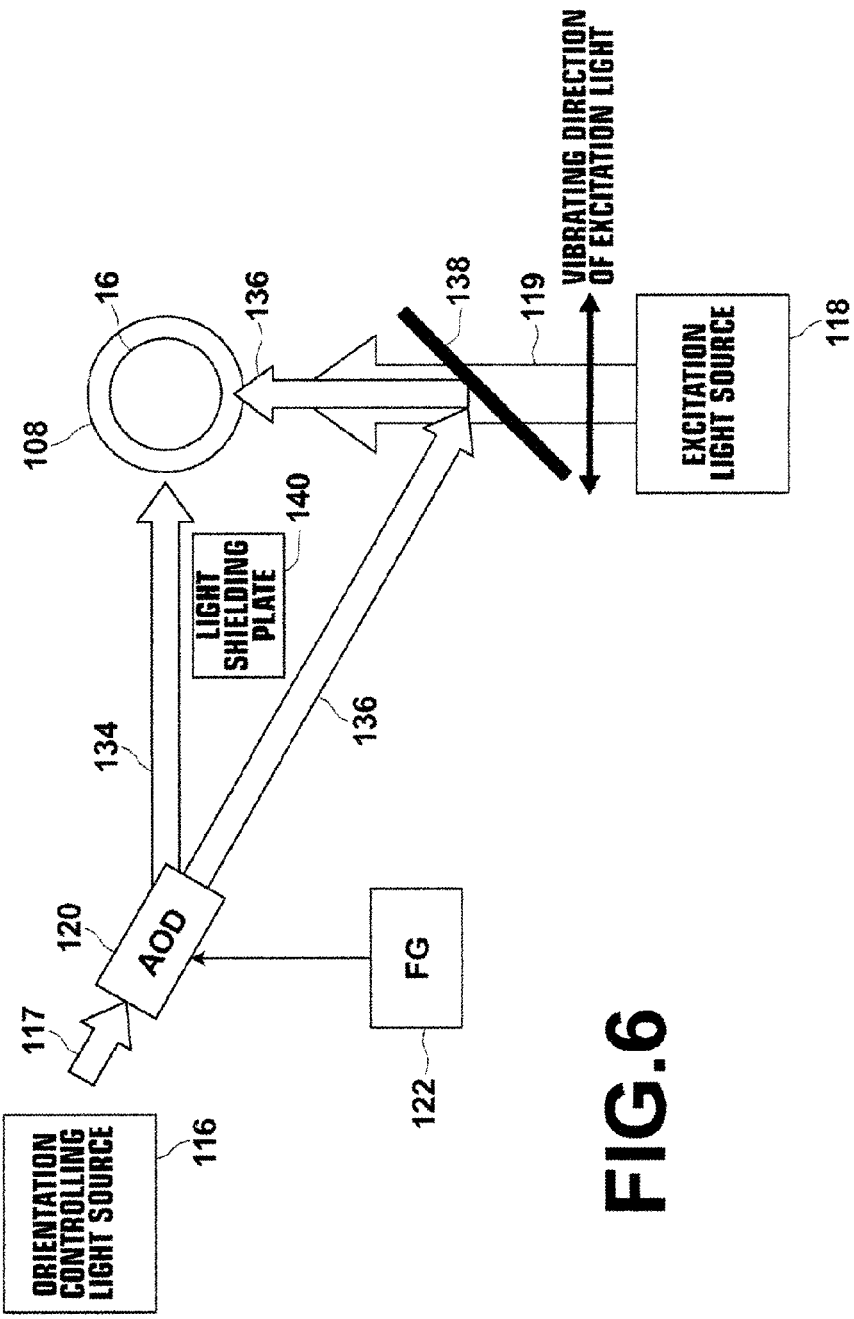
FIG. 6 is a schematic plan view that illustrates switching of the emission direction of orientation controlling light beams emitted by an orientation controlling light source.

FIG. 6 is a schematic plan view of the interior of the biological molecule detecting apparatus 100 that illustrates switching of the emission direction of the laser beam emitted by the orientation controlling light source 116.

The orientation controlling light beam 117 emitted from the orientation controlling light source 116 passes through the AOD 120 and enters the reagent cup 108. The orientation controlling light beam 117 emitted by the orientation controlling light source 116 is of a width that enables the entirety of the solution within the reagent cup 108 to be irradiated thereby.

The AOD 120 alternately switches the direction that the orientation controlling light beam 117 emitted from the orientation controlling light source 116 propagates between two directions. Specifically, the AOD 120 causes the orientation controlling light beam 117 to propagate in the direction of the arrow 134 in the case that a 5V orientation control signal is input thereto, and causes the orientation controlling light beam 117 to propagate in the direction of the arrow 136 in the case that a 0V orientation control signal is input thereto.

The orientation controlling light beam 117 that propagates in the direction of the arrow 134 enters the side surface of the reagent cup 108. The orientation controlling light beam 117 that propagates in the direction of the arrow 136 is reflected by the dichroic mirror 138, propagates in a direction perpendicular to the arrow 134, and enters the side surface of the reagent cup 108. If the reagent cup 108 viewed from above is considered as a clock face, the orientation controlling light beam 117 that propagates in the direction of the arrow 134 enters from the 9 o'clock position and propagates toward the 3 o'clock position, whereas the orientation controlling light beam 117 that propagates in the direction of the arrow 136 enters from the 6 o'clock position and propagates toward the 12 o'clock position. That is, the direction in which the orientation controlling light beam 117 that propagates in the direction of the arrow 134 enters the reagent cup 108 and the direction in which the orientation controlling light beam 117 that propagates in the direction of the arrow 136 enters the reagent cup 108 are perpendicular to each other.

The dichroic mirror 138 only reflects light having the wavelength of the orientation controlling light beam 117, and transmits light having other wavelengths. The excitation light 119 emitted from the excitation light source 118 passes through the dichroic mirror 138, propagates in the same direction as the orientation controlling light beam 117 reflected by the dichroic mirror 138, and enters the side surface of the reagent cup 108.

This configuration enables the biological molecule detecting apparatus 100 to alternately switch the direction in which the laser beam enters the reagent cup 108 between two directions which are 90 degrees different from each other, by controlling the AOD 120 according to the input of the orientation control signals from the FG 122.

A light shielding plate 140 is placed between the AOD 120 and the reagent cup 108, and the biological molecule detecting apparatus 100 is configured such that laser beams that propagate in directions other than those indicated by the arrow 134 and the arrow 136 do not enter the reagent cup 108. In addition, the orientation controlling light beam 117 enters the side surface of the cylindrical reagent cup 108 both in the case that it propagates in the direction of the arrow 134 and in the direction of the arrow 136. Because the reagent cup 108 is cylindrical, the shape of the side surface of the reagent cup 108 that the orientation controlling light beam 117 enters is the same even if the direction that the laser propagates in is switched.

The motion of fluorescent molecules within the reagent cup 108 in response to the switching of the emission direction of the orientation controlling light beam 117 will be described with reference to FIG. 7A and FIG. 7B. FIG. 7A is a schematic diagram that illustrates the relationship between a first orientation controlling light beam 117 emission direction and the orientation direction of a molecule. FIG. 7B is a schematic diagram that illustrates the relationship between a second orientation controlling light beam 117 emission direction and the orientation direction of a molecule. FIG. 7A and FIG. 7B are plan views of the reagent cup 108. Note that in the present specification, the "orientation direction" of the free molecules and the binding molecules refers to a direction in which the antibodies and the fluorescent molecules are oriented after orientation thereof is completed.

The binding molecules 15 within the reagent cup 108 into which the orientation controlling light beam 117 is emitted become oriented in a specific direction by receiving the external force of the orientation controlling light beam 117. The external force exerted by the orientation controlling light beam 117 is generated by reactions to the laser beam hitting the binding molecules and being scattered. The direction in which the force is exerted is determined by the direction in which the laser beam is propagating and the orientations (the direction in which the fluorescent molecule 14, the antibody 12, and the antigen 18 are arranged) of the binding molecules.

Normally, the free molecules and the binding molecules are dispersed within the solution, oriented in random directions. However, binding molecules 15 irradiated by the orientation controlling light beam 117 that propagates from the left to the right of the drawing sheet receive force in a rotational direction from the orientation controlling light beam 117 that propagates in the direction of the arrow 134, and stabilize in an orientation in a direction in which the external forces in various rotational direction imparted by the orientation controlling light beam 117 balance out within the range that the orientation controlling light beam 117 is irradiated, as illustrated in FIG. 7A. In other words, the binding molecules 15 receive external force to rotate in the rightward or leftward direction in cases that the longitudinal direction thereof is not the same as the direction in which the orientation controlling light beam 117 propagates. However, in the case that the longitudinal directions of the binding molecules 15 are the same as the direction in which the orientation controlling light beam 117 propagates, the external rotational force in the rightward or leftward direction balance out, and therefore the binding molecules stabilize. The binding molecules 15 within the reagent cup 108 all become oriented in the same direction (a direction in which the direction that the orientation controlling light beam 117 propagates in and the longitudinal directions of the binding molecules 15 are parallel). That is, the transition moments of the fluorescent molecules 14 associated with all of the binding molecules 15 will be aligned in the same direction. Meanwhile, the free molecules 13 within the reagent cup 108 are not oriented because forces that cause Brownian motion are greater than the external force exerted by the orientation controlling light beam 117, and undergo Brownian motion within the solution.

When the direction that the orientation controlling light beam 117 propagates in is switched from the horizontal direction of the drawing sheet to the vertical direction of the drawing sheet as illustrated in FIG. 7B, the binding molecules 15 which had been oriented toward the right of the drawing sheet will receive forces to rotate toward the left. The binding molecules 15 that receive the orientation controlling light beam 117 that propagates from the bottom of the drawing sheet to the top of the drawing sheet are oriented in a direction perpendicular to the direction that they were oriented by the orientation controlling light beam 117 that propagated from the left to the right of the drawing sheet, and stabilize. In this case as well, the transition moments of the fluorescent molecules 14 associated with all of the binding molecules 15 will be aligned in the same direction. The free molecules 13 within the reagent cup 108 are not oriented because forces that cause Brownian motion are greater than the external force exerted by the orientation controlling light beam 117, and undergo Brownian motion within the solution. The orientation direction of the binding molecules 15 within the solution can be switched by changing the emission direction of the orientation controlling light beam 117 in this manner.

In the present embodiment, the directions of the transition moments of the fluorescent molecules 14 which have been oriented by the orientation controlling light beam 117 that propagates in the direction of the arrow 134 are parallel to the direction in which the linearly polarized excitation light vibrates, maximizing the excitation efficiency of the fluorescent molecules 14. Meanwhile, the directions of the transition moments of the fluorescent molecules 14 which have been oriented by the orientation controlling light beam 117 that propagates in the direction of the arrow 136 are perpendicular to the direction in which the linearly polarized excitation light vibrates, and the excitation efficiency of the fluorescent molecules 14 is 0. Accordingly, switching of the emission direction of the orientation controlling light beam 117 by the AOD 120 switches the excitation efficiency of the fluorescent molecules 14 with respect to the linearly polarized excitation light between a maximum and a minimum (in which excitation does not occur). In the case that the orientation control signal input to the AOD 120 is 5V, the excitation efficiency of the fluorescent molecules 14 associated with the binding molecules 15 becomes maximal, and in the case that the orientation control signal input to the AOD 120 is 0V, the excitation efficiency of the fluorescent molecules 14 associated with the binding molecules 15 becomes minimal.

Next, the detailed structure of the light receiving section 124 will be described with reference to FIG. 8. FIG. 8 is a schematic diagram that illustrates the detailed structure of the light receiving section 124. The light receiving section 124 includes: a lens 142; a filter 144; a polarizing element 146; a lens 148; and a PD (photodiode) 150. The light receiving section 124 receives fluorescence from the bottom side of the reagent cup 108.

Fluorescence 147 emitted by the fluorescent molecules 14 within the reagent cup 108 and enters the light receiving section 124 toward the left side of the drawing sheet, and fluorescence 149 emitted by the fluorescent molecules 14 and enters the light receiving section 124 toward the right side of the drawing sheet are focused and collimated by the lens 142, then enter the PD 150 after passing through the filter 144, the polarizing element 146, and the lens 148. Note that although not illustrated in FIG. 8, fluorescence is present between the fluorescence 147 and the fluorescence 149. However, the behavior of such fluorescence is predictable by those skilled in the art, and therefore a description thereof will be omitted.

The filter 144 is a band pass filter that cuts off light other than the fluorescence emitted by the fluorescent molecules 14, and prevents light other than the fluorescence, such as the excitation light, from entering the PD 150.

The polarizing element 146 only transmits light which is polarized in the same direction as the vibration direction of the linearly polarized excitation light 119. The excitation light which is scattered within the reagent cup 108 and fluorescence emitted by the fluorescent molecules 14 while the directions of the orientations of the free molecules and the binding molecules are being switched have vibration directions different from the original vibration direction of the excitation light, and therefore cannot be transmitted through the polarizing element 146.

The PD 150 is constituted by an APD (Avalanche Photodiode). The PD 150 receives the fluorescence focused by the lens 148, generates electric charges corresponding to the intensity of the fluorescence focused by the lens 148, and outputs the electrical charges to the amplifier 126.

The light receiving section 124 converts the fluorescence emitted by the fluorescent molecules 14, of which the orientations have been switched, into electrical charges in this manner. In addition, the light receiving section 124 receives the fluorescence from the bottom side of the reagent cup 108. Therefore, the light receiving section 124 is not likely to be influenced by the orientation controlling light beam 117 and the excitation light 119. In the present embodiment, The PD 150 receives the fluorescence which is focused by the lens 148, generates electrical charges corresponding to the intensity of the fluorescence, and outputs the generated electrical charges to the amplifier 126. The light receiving section 124 converts the fluorescence emitted by the fluorescent molecules 14 of which the orientations have been switched into electrical charges in this manner. In addition, the light receiving section 124 receives the fluorescence toward the bottom side of the reagent cup 108. Therefore, the light receiving section 124 is not likely to be influenced by the orientation controlling light beam 117 and the excitation light 119. In the present specification, that "switching of the orientation is completed" refers to a state in which the molecules are in a stable state with respect to the external force exerted by the orientation controlling light beam after switching of the emission direction of the orientation controlling light beam.

Figure 9:
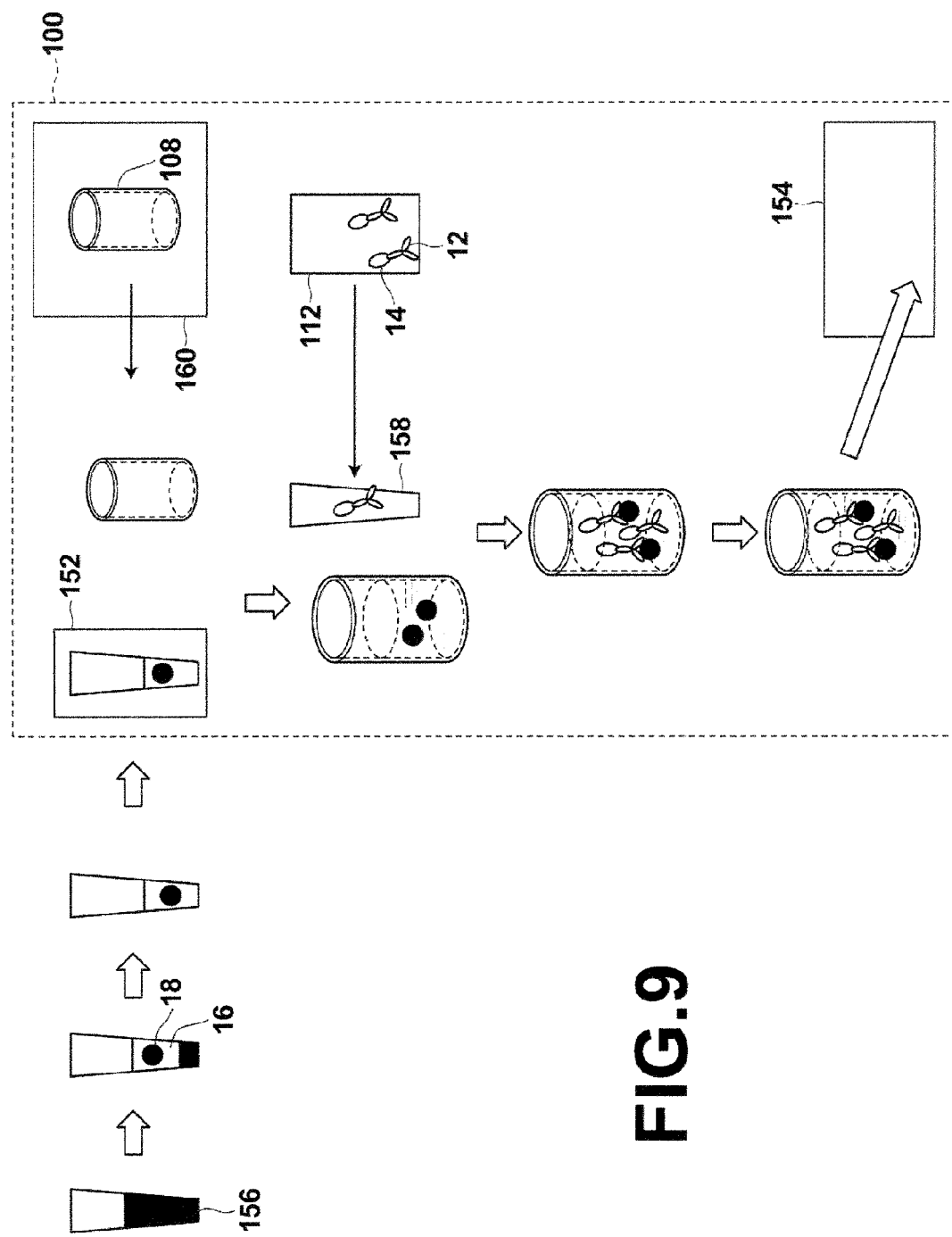
FIG. 9 is a diagram that schematically illustrates the flow of a process from preparation of a sample through disposal thereof.

Next, the operations of the biological molecule detecting apparatus 100 during measurements will be described. FIG. 9 is a diagram that schematically illustrates the flow of a process from preparation of a sample through disposal thereof.

To prepare for measurement, first, 50 µL of whole blood 156 collected from a patient is centrifugally separated to separate plasma 16. The separated plasma 16 is set in a sample setting section of the biological molecule detecting apparatus 100. The steps up to this point are performed by a user.

The biological molecule detecting apparatus 100 dispenses the plasma 16, which is set in a sample setting section 152, into a new reagent cup 108, which is stocked in a reagent cup stocking section 160. Next, the biological molecule detecting apparatus 100 suctions PSA antibodies, which are in the reagent tank 112, with a pipette 158, and dispenses the suctioned PSA antibodies into the reagent cup 108. The biological molecule detecting apparatus 100 which has placed the plasma 16 and the PSA antibodies into the reagent cup 108 uses a built in vortex mixer to agitate the reagent cup 108 while maintaining the temperature of the reagent cup 108 at 37° C. to cause antigen antibody reactions to occur. Thereafter, the biological molecule detecting apparatus 100 emits excitation light, detects fluorescence, and disposes of the reagent cup 108 into a built in trash receptacle 154 after the fluorescence is detected.

Examples of the orientation control signals output by the FG 122 and the PD outputs output by the PD 150 are illustrated in FIG. 10A. An example of lock in amplifier outputs output by the lock in amplifier 127 is illustrated in FIG. 10B. Note that here, the graphs of the PD outputs and the lock in amplifier outputs are illustrated schematically in order to simplify the description.

The orientation control signal output by the FG 122 is 0V prior to measurement. The orientation control signal is a square wave having a period of 2T that outputs a signal of 5V from 0 to T (seconds) and outputs a 0V signal from T to 2T (seconds). Prior to measurement, the orientation control signal is 0V, and therefore the orientation controlling light beam 136 is emitted onto the reagent cup 108, and all of the binding molecules are oriented in the same direction.

The biological molecule detecting apparatus 100 switches the orientation control signal to 5V at a time T1, and emits the excitation light toward the reagent cup 108. Thereafter, when the orientation control signal becomes 5V, the AOD 120 switches the direction in which the orientation controlling light beam 117 propagates, and the direction in which the orientation controlling light beam 117 propagates is switched from the direction of the arrow 136 to the direction of the arrow 134. Accompanying the switch in the direction that the orientation controlling light beam 117 propagates in, the direction in which the orientation controlling light beam 117 is emitted with respect to the reagent cup 108 is also switched 90 degrees.

Accompanying the switch in the emission direction of the laser beam, the orientation direction of the binding molecules 15 is also switched. Fluorescence 123 is emitted when the directions of the transition moments of the fluorescent molecules and the vibration direction of the excitation light beam 119 become non perpendicular. Most of the fluorescence emitted by the fluorescent molecules 14 associated with the binding molecules 15 during the switch in orientation is not polarized, and therefore is cut off by the polarizing element 146.

The fluorescent molecules 14 associated with the binding molecules 15 which have completed the switch in orientation have transition moments which are parallel to the vibration direction of the excitation light 119, and therefore the excitation efficiency thereof becomes maximal. The fluorescence emitted by the fluorescent molecules 14 associated with the binding molecules 15 which have completed the switch in orientation is polarized in the same direction as the polarization direction of the excitation light, and therefore reach the PD 150 without being cut off by the polarizing element 146.

At the moment of time T1 when the excitation light 119 is irradiated onto the reagent cup 108, the PD output is a value of iz. The PD output iz is a value that includes fluorescence emitted by the fluorescent molecules 14 associated with a portion of the free molecules 13 within the solution, noise inherent to the apparatus, etc. The fluorescent molecules 14 associated with the binding molecules 15 are not excited when the orientation control signal is 0V, and therefore do not contribute to the PD output.

The PD output increases from iz, by the fluorescence 123 emitted by the fluorescent molecules 14 associated with the binding molecules 15, which have completed the switch in orientation due to the orientation control signal changing from 0V to 5V, reaching the PD. Most of the fluorescence 123 emitted by the fluorescent molecules 14 associated with the binding molecules 15 during the switch in orientation is not polarized, and therefore is cut off by the polarizing element 146. The PD output increases as the number of binding molecules 15 which have completed the switch in orientation increases, and becomes saturated as a value it when the switch in orientation of all of the binding molecules 15 is completed.

The orientation control signal becomes 0V after the output of 5V is continued for T seconds. T seconds is a period of time greater than or equal to at least the amount of time required for all of the binding molecules 15 to complete the switch in orientation. That is, T seconds is a period of time greater than or equal to the amount of time required for the PD output to become saturated at the value it. When the switch in orientation is completed for all of the binding molecules 15 and time T2 is reached, the orientation control signal changes from 5V to 0V. When the orientation control signal changes from 5V to 0V, the directions of the transition moments of the fluorescent molecules 14 associated with the binding molecules 15 and the vibration direction of the excitation light 119 become perpendicular, the excitation efficiency of the fluorescent molecules 14 associated with the binding molecules 15 becomes 0, and fluorescence 123 is no longer emitted. Therefore, the PD output gradually decreases until it becomes iz. In this case as well, most of the fluorescence 123 emitted by the fluorescent molecules 14 associated with the binding molecules 15 during the switch in orientation is not polarized, and therefore is cut off by the polarizing element 146.

After a time T elapses from time T2 and the orientation control signal becomes 5V again at time T3, the PD output increases and becomes saturated at the value it. Here, the period of time that the orientation control signal was set to 0V was set to be T seconds, which is the same period of time that the orientation control signal was set to 5V. This is because under conditions that the output of the orientation controlling light beam 117 is constant, the amount of time required for the switch in orientation of the binding molecules 15 within the solution to become complete is approximately the same for a case in which the orientation control signal is changed from 0V to 5V and for a case in which the orientation control signal is changed from 5V to 0V.

After a time T elapses from time T3 and the orientation control signal becomes 0V at time T4, the PD output decreases and becomes the value iz. Note that a single period of the orientation control signal is 2T. Therefore, T4−T3=T3−T2=T2−T1=T. That is, the PD output periodically repeats increases and decreases in value at a period 2T in the same manner as the orientation control signal.

The lock in amplifier 127 detects components that repeat increases and decreases synchronized with a reference signal from among signals input thereto. In the biological molecule detecting apparatus 100, signals which are the same as the orientation control signal are input to the lock in amplifier 127 as the reference signal. That is, the lock in amplifier 127 detects components synchronized with the orientation control signal from the PD output. The PD output is a periodic signal that repeats increases and decreases in value at a period 2T. The fluorescence emitted by the fluorescent molecules 14 associated with the binding molecules 15 contribute to the periodic components of the PD output. Accordingly, the contribution of the binding molecules 15 can be extracted from the PD output, by extracting the components which are synchronized with the orientation control signal. The output of the lock in amplifier 127 is an unstable output that repeats increases and decreases at first, but gradually converges to a value S. The value S is the PD output of the total amount of fluorescence emitted by the fluorescent molecules 14 associated with the binding molecules 15.

The CPU 132 calculates the concentration C of the detection target substance from the lock in amplifier output S. Specifically, the concentration C is calculated according to Formula (I) below.

$$C = f(S) \quad (1)$$

Here, f(S) is a calibration curve function. The biological molecule detecting apparatus 100 has different calibration curve functions for each item to be measured prepared in advance, and converts the measurement value S to the concentration C. The CPU 132 outputs the obtained concentration C to the display section 102.

As described above, the biological molecule detecting apparatus 100 according to the first embodiment of the present invention is of a configuration that switches the emission direction of the orientation controlling light beam 117, thereby enabling switching of the orientation directions of the binding molecules 15 within the solution. The directions in which the binding molecules 15 are oriented by the orientation controlling light beam 117 are that in which the transition moments of the fluorescent molecules 14 associated with the binding molecules 15 are parallel to the vibration direction of the linearly polarized excitation light, and that in which the transition moments of the fluorescent molecules 14 associated with the binding molecules 15 are perpendicular to the vibration direction of the linearly polarized excitation light. That is, the biological molecule detecting apparatus 100 is capable of switching between a state in which the fluorescent molecules 14 associated with the binding molecules 15 are capable of being excited by the excitation light and a state in which the fluorescent molecules 14 associated with the binding molecules 15 are not capable of being excited by the excitation light.

The lock in amplifier 127 detects components, which are synchronized with the orientation control signal that command switching of the emission direction of the orientation controlling light beam 117, from among the received fluorescence data. Therefore, the contribution of the fluorescent molecules associated with the binding molecules 15 which are oriented by the orientation controlling light beam 117 can be calculated, and the concentration of the detection target substance can be accurately measured with a simple structure.

In the configuration described above, the biological molecule detecting apparatus 100 switches the orientations of all of the binding molecules into the same direction by the external force exerted by the orientation controlling light beam 117. Therefore, measurements having higher sensitivity can be performed compared to cases in which measurements are performed utilizing Brownian motion, which is random.

Note that in the present embodiment, Alexa Fluor 568 was employed as the fluorescent molecules. However, the fluorescent molecules to be employed by the present invention are not limited to Alexa Fluor 568. Any fluorescent molecule may be employed, as long as it has a transition moment, is excited by excitation light, and emits light capable of being detected by the PD.

Note that the present embodiment was described as a case in which antigen antibody reactions are utilized as an example. However, the combination of the detection target substance and the substance that specifically binds with the detection target substance is not limited to the case described above. For example, the present invention may be applied to cases in which antigens are employed to detect antibodies, cases in which a specific nucleic acid is employed to detect a nucleic acid that hybridizes with the specific nucleic acid, cases in which nucleic acids are employed to detect nucleic acid binding proteins, cases in which ligands are employed to detect receptors, cases in which sugars are employed to detect lectin, cases in which protease detection is utilized, cases in which higher order structure changes are utilized, etc.

In addition, it is desirable for the period of time during which the orientation control signal is set to 5V or 0V to be changed, based on the volumes and molecular weights of the binding molecules, the viscosity of the solution, the temperature of the solution, etc. The amount of time required for reorientation of the binding molecules to become complete following switching of the emission direction of the orientation controlling light beam 117 is determined by the ease with which the binding molecules rotate within the solution, which is influenced by the molecular weights and volumes of the binding molecules, the viscosity of the solution, the temperature of the solution, etc. In cases that it is difficult for the binding molecules to rotate within the solution, the amount of time required for reorientation of the binding molecules to be completed will become longer. Therefore, it is desirable for the period of time during which the orientation control signal is set to 5V or 0V to be long enough for reorientation to be completed. It is desirable for the period of time that the orientation control signal is set to 5V or 0V to be longer as the molecular weight of the binding molecules is greater, and for the period of time that the orientation control signal is set to 5V or 0V to be shorter as the molecular weight of the binding molecules is smaller.

In addition, the first embodiment employed a laser beam having a wavelength of 980 nm and an output of 700 mW as the orientation controlling light beam 117. However, laser beam to be employed as the orientation controlling light beam 117 is not limited to such a laser beam. It is desirable for the wavelength and the output of the orientation controlling light beam 117 to be determined based on the ease with which the free molecules and the binding molecules rotate within the solution, which is influenced by the volumes of the free molecules and the binding molecules, the molecular weights of the free molecules and the binding molecules, the viscosity of the solution, the absolute temperature of the solution, etc. such that the output light beam only orients the binding molecules.

Second Embodiment

Figure 11A:
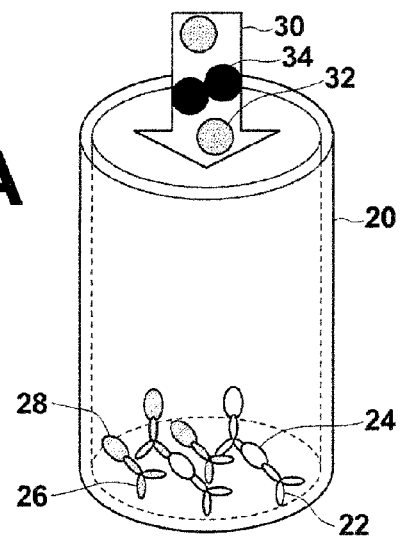
FIG. 11A is a first schematic diagram that illustrates antigen antibody reactions in a biological molecule detecting apparatus according to a second embodiment.
Figure 11B:
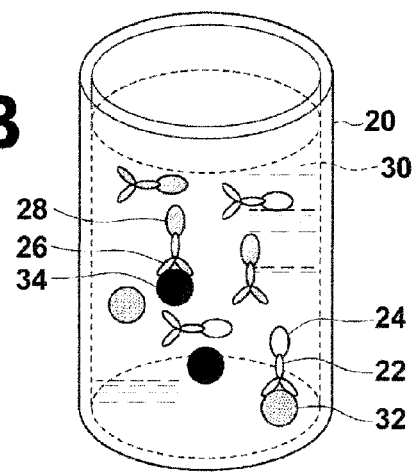
FIG. 11B is a second schematic diagram that illustrates antigen antibody reactions in the biological molecule detecting apparatus according to the second embodiment.

FIGS. 11A and 11B are schematic diagrams that illustrate antigen antibody reactions in a biological molecule detecting apparatus according to a second embodiment. The second embodiment utilizes two types of antibodies to detect two types of antigens within a single solution.

Hereinafter, a case will be considered in which antibodies 22 and antibodies 26 are placed within a reagent cup 20. The antibodies 22 and the antibodies 26 are labeled with fluorescent molecules 24 and fluorescent molecules 28, respectively.

When a sample 30 is placed in the reagent cup 20 and agitated, and if antigens 32 that specifically bind with the antibodies 22 are present in the in the sample 30, antigen antibody reactions will occur between the antibodies 22 and the antigens 32. Similarly, if antigens 34 that specifically bind with the antibodies 26 are present in the in the sample 30, antigen antibody reactions will occur between the antibodies 26 and the antigens 34.

In the same manner as that described with respect to the first embodiment, a portion of the antibodies and the antigens remain within the sample solution without undergoing antigen antibody reactions. Hereinafter, the antibodies 22, the antigens 32, and the fluorescent molecules 24 which are bound to each other by antigen antibody reactions will be referred to as binding molecules 1, and the antigens 22 and the fluorescent molecules 24 which have not undergone antigen antibody reactions but are present in the liquid will be referred to as free molecules 1. Further, the antibodies 26, the antigens 34, and the fluorescent molecules 28 which are bound to each other by antigen antibody reactions will be referred to as binding molecules 2, and the antibodies 26 and the fluorescent molecules 28 which have not undergone antigen antibody reactions but are present in the liquid will be referred to as free molecules 2. In the present embodiment, the antigens 32 and the antigens 34, which are detection target substances, are PSA and SCC (Squamous Cell Carcinoma) antigens, respectively. PSA antibodies that specifically bind to PSA are employed as the antibodies 22, and SCC antibodies that specifically bind to SCC are employed as the antibodies 26. Alexa Fluor 568 by Molecular Probes is employed as the fluorescent molecules 24, and Alexa Fluor 555 by Molecular Probes is employed as the fluorescent molecules 28. Alexa Fluor 555 emits fluorescence having wavelengths within a range from 540 nm to 700 nm, and emits fluorescence having a wavelength of approximately 570 nm most intensely.

The biological molecule detecting apparatus according to the second embodiment of the present invention emits excitation light onto the solution, in which the two types of free molecules and the two types of binding molecules are present, and detects or quantifies target binding molecules.

Figure 12:
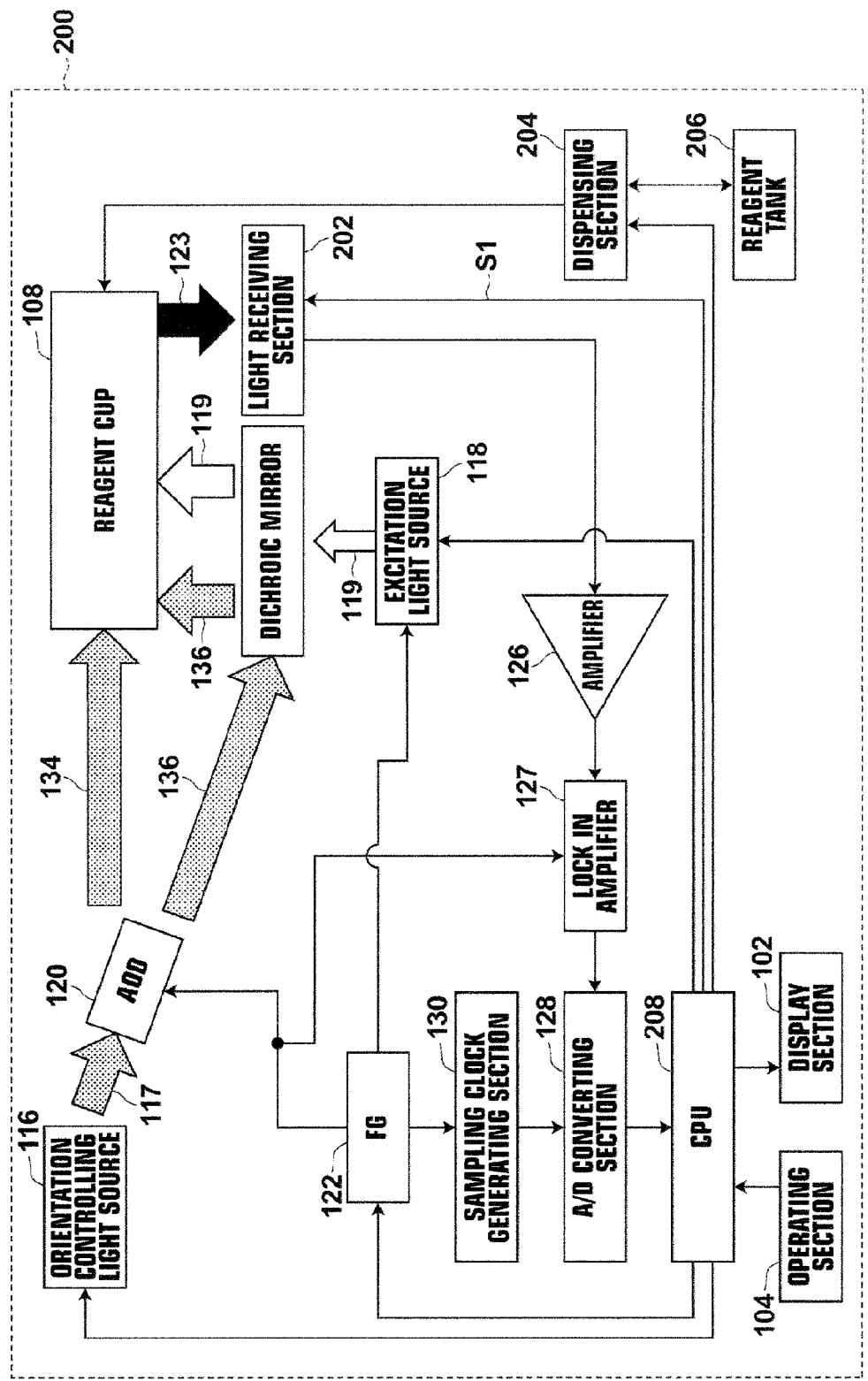
FIG. 12 is a block diagram that illustrates the main components of the biological molecule detecting apparatus according to the second embodiment.

FIG. 12 is a block diagram that illustrates the main components of the biological molecule detecting apparatus 200 according to the second embodiment. Note that constituent elements of the biological molecule detecting apparatus 200 which are the same as those of the biological molecule detecting apparatus 100 of the first embodiment are denoted with the same reference numerals, and detailed descriptions thereof will be omitted.

The biological molecule detecting apparatus 200 is different from the biological molecule detecting apparatus 100 of the first embodiment in the configurations of a light receiving section 202, a dispensing section 204, a reagent tank 206, and a CPU 208.

The dispensing section 204 suctions two types of antibodies from the reagent tank 206, which stores a plurality of antibodies in separate containers, and dispenses the suctioned antibodies into the reagent cup 108.

The light receiving section 202 detects fluorescence emitted by the fluorescent molecules within the reagent cup 108. The light receiving section 202 is configured to receive fluorescence emitted by the fluorescent molecules 24 and fluorescence emitted by the fluorescent molecules 28 separately in response to commands (S1) from the CPU 208.

The CPU 208 performs calculations on digital data output thereto from the A/D converting section 128, and outputs the results of calculation to the display section 102. In addition, the CPU 208 controls the operations of the orientation controlling light source 116, the excitation light source 118, the dispensing section 204, the FG 122, and the light receiving section 202, in response to commands input from the user input section 104. Specifically, the CPU 208 outputs ON/OFF commands to the orientation controlling light source 116 and the excitation light source 118, outputs commands that specify reagents to be utilized and commands to initiate dispensing operations to the dispensing section 204, outputs commands that specify the waveform of voltage signals to be output and commands to output the voltage signals to the FG 122, and outputs commands to switch filters to the light receiving section 202.

The configuration of the light receiving section 202 will be described in detail with reference to FIG. 13. FIG. 13 is a schematic diagram that illustrates the detailed structure of the light receiving section 202 of the biological molecule detecting apparatus 200 according to the second embodiment. A filter switching section 210 within the light receiving section 202 is equipped with two types of filters, a filter 212 and a filter 214. The two filters are movable, and the filter switching section 210 is configured to enable switching of the filter through which light focused and collimated by the lens 142 passes.

Fluorescence 216 emitted by the fluorescent molecules 14 within the reagent cup 108 and enters the light receiving section 202 toward the left side of the drawing sheet, and fluorescence 218 emitted by the fluorescent molecules 14 and enters the light receiving section 202 toward the right side of the drawing sheet are focused and collimated by the lens 142, then enter the PD 150 after passing through the filter 212 or the filter 214, the polarizing element 146, and the lens 148. Note that although not illustrated in FIG. 13, fluorescence is present between the fluorescence 216 and the fluorescence 218. However, the behavior of such fluorescence is predictable by those skilled in the art, and therefore a description thereof will be omitted.

The filter switching section 210 switches the filter to be utilized in response to commands output thereto from the CPU 208. In the present embodiment, a light receiving side filter of a SpRed-A filter set by Semrock is employed as the filter 212. The light receiving side filter of the SpRed-A filter set is a band pass filter that transmits wavelengths within a range from 605 nm to 650 nm. Meanwhile, a light receiving side filter of a SpOr-A filter set by Semrock is employed as the filter 214. The light receiving side filter of the SpOr-A filter set is a band pass filter that transmits wavelengths within a range from 575 nm to 600 nm.

Next, the operations of the biological molecule detecting apparatus 200 during measurements will be described. The measurement operations of the biological molecule detecting apparatus 200 are basically the same as the measurement operations of the biological molecule detecting apparatus 100 of the first embodiment, but differ in fine points. The principle behind detecting the free molecules and the binding molecules separately was described with respect to the first embodiment, and therefore how the two types of binding molecules are detected separately will be described here.

First, the biological molecule detecting apparatus 200 determines which of the two types of binding molecules are to be detected. This determination may be performed as desired, by user input via the user input section 104, for example. Here, a case will be described in which the binding molecules 1 having Alexa Fluor 568 as fluorescent molecules are detected first will be described. The CPU 208 outputs a command that instructs the filter switching section 210 within the light receiving section 202 to utilize the filter 212. The filter switching section 210 receives the command from the CPU 208, and moves the filter 212 to a position at which light focused and collimated by the lens 142 passes. When the orientation control signal is changed to 5V and excitation light is emitted toward the reagent cup 108, fluorescence is emitted by the fluorescent molecules 24 and the fluorescent molecules 28 within the solution. The fluorescence emitted by the fluorescent molecules 24 and the fluorescent molecules 28 is focused and collimated by the lens 142 and enters the filter 212. The filter 212 only transmits light having wavelengths within a range from 605 m to 650 nm. Therefore, the fluorescence emitted by the fluorescence molecules 24 passes through the filter 212, while the fluorescence emitted by the fluorescent molecules 28 is substantially completely cut off. Only the fluorescence emitted by the fluorescent molecules 24 can be detected in this manner.

In the same manner as in the first embodiment, measurements are performed by the biological molecule detecting apparatus 200 for several periods of the orientation control signal. The PD output resulting from detecting fluorescence emitted by the fluorescent molecules 24 is illustrated in FIG. 14A. Note that here, the graph of FIG. 14A is illustrated schematically in order to simplify calculations. The PD output is a signal having the same period as the period of the orientation control signal. Although not shown in FIG. 14A, the lock in amplifier detects components which are synchronized with the period of the orientation control signal from the PD output, and outputs a value S1.

Next, the CPU 208 calculates the concentration of the binding molecules 1 from the value S1. Specifically, a calibration curve function f1 (S) is employed to convert the value S1 to a concentration C1 in the same manner as in the first embodiment. The CPU 208 outputs the obtained concentration C2 to the display section 102.

Next, the biological molecule detecting apparatus 200 performs measurement of the binding molecules 2. The CPU 208 outputs a command that instructs the filter switching section 210 within the light receiving section 202 to utilize the filter 214. The filter switching section 210 receives the command from the CPU 208, and moves the filter 214 to a position at which light focused and collimated by the lens 142 passes. The filter 214 only transmits light having wavelengths within a range from 575 m to 600 nm. Therefore, the fluorescence emitted by the fluorescence molecules 24 is shielded by the filter 214, while the fluorescence emitted by the fluorescent molecules 28 is transmitted therethrough. Only the fluorescence emitted by the fluorescent molecules 28 can be detected in this manner.

Measurements are performed by the biological molecule detecting apparatus 200 for several periods of the orientation control signal. The PD output resulting from detecting fluorescence emitted by the fluorescent molecules 28 is illustrated in FIG. 14B. Note that here, the graph of FIG. 14B is illustrated schematically in order to simplify calculations. The PD output is a signal having the same period as the period of the orientation control signal.

The timings at which the orientation control signals are switched when the binding molecules 2 are measured are different from those when the binding molecules 1 are measured. This is because the volumes and molecular weights of the binding molecules 1, the free molecules 1, the binding molecules 2, and the free molecules 2 are different, and the amounts of time required for orientation of the molecules to be completed differ.

As illustrated in FIG. 14A and FIG. 14B, the timings at which the PD outputs switch from increase to decrease are the same for a case in which the binding molecules 1 are measured and a case in which the binding molecules 2 are measured. However, the maximum value and the minimum value of the PD outputs are different. This is due to the difference in concentrations of the binding molecules 1 and the binding molecules 2 within the solution, and the difference in concentrations of the free molecules 1 and the free molecules 2 within the solution.

Next, the CPU 208 calculates the concentration of the binding molecules 2 from a value S2. Specifically, a calibration curve function f2 (S) is employed to convert the value S2 to a concentration C2. The CPU 208 outputs the obtained concentration C1 to the display section 102.

As described above, the biological molecule detecting apparatus 200 according to the second embodiment of the present invention employs two types of antibodies and fluorescent molecules as substances that specifically bind with detection target substances and is equipped with the filter switching 210 which enables switching between two types of filters, in addition to having the structures of the biological molecule detecting apparatus 100 of the first embodiment. Thereby, only fluorescence emitted by the fluorescent molecules associated with the binding molecules that include a detection target substance can be detected, by utilizing a filter corresponding to the fluorescent molecules associated with the binding molecules that include the detection target substance. Accordingly, the concentrations of two types of detection target substances which are included in a single sample can be accurately measured.

Note that Alexa Fluoro 568 and Alexa Fluoro 555 were employed as the fluorescent molecules in the present embodiment. However, the fluorescent molecules are not limited to these. A plurality of substances that specifically bind to a plurality of detection target substances respectively may be labeled with a plurality of types of fluorescent molecules having fluorescent wavelengths which are sufficiently different to be capable of being separated by filters.

Note that the present embodiment was described as a case in which antigen antibody reactions are utilized as an example. However, the combination of the detection target substance and the substance that specifically binds with the detection target substance is not limited to the case described above. For example, the present invention may be applied to cases in which antigens are employed to detect antibodies, cases in which a specific nucleic acid is employed to detect a nucleic acid that hybridizes with the specific nucleic acid, cases in which nucleic acids are employed to detect nucleic acid binding proteins, cases in which ligands are employed to detect receptors, cases in which sugars are employed to detect lectin, cases in which protease detection is utilized, cases in which higher order structure changes are utilized, etc.

In addition, the second embodiment was described as a case in which two types of detection target substances are utilized. However, the number of detection target substances is not limited to two. In such cases as well, each of the detection target substances can be detected separately, by employing a plurality of substances that specifically bind with each of the plurality of detection target substances, labeling each of the plurality of specific binding substances with a different type of fluorescent molecules, and detecting the fluorescence emitted by each type of fluorescent molecule by separating the fluorescence with a plurality of filters corresponding to each type of fluorescent molecule.

Note that the number of types of fluorescent molecules will increase as the number of types of detection target substances increases, and fluorescence emitted by the plurality of types of fluorescent molecules will be present, and there may be cases in which it is difficult to separate the fluorescence using only filters. In such cases, the types of excitation light may be increased to facilitate separate the fluorescence. The degrees of light absorption of fluorescent molecules depend on the wavelength of excitation light, and each type of fluorescent molecule has a wavelength band which is easily absorbed. For this reason, changing the wavelength of the excitation light causes only a portion of the fluorescent molecules to emit fluorescence, facilitating separation of the fluorescence using filters. In addition, detection of fluorescence emitted by target fluorescent molecules can be facilitated by employing band pass filters having narrower passbands.

In addition, filters were employed as the spectral separating means for spectrally separating light at the light receiving section in the present embodiment. However, it is not necessary to spectrally separate light using filters. For example, only light having specific wavelengths may be received by the photodiode, by spectrally separating light using a diffraction grating or a prism.

(Design Modifications to the First and the Second Embodiments)

Note that the embodiments of the present invention described above are merely examples of the present invention, and do not limit the structure of the present invention. The biological molecule detecting apparatus of the present invention is not limited to the embodiments described above, and various changes and modifications are possible as long as they do not stray from the objective of the present invention.

For example, the external force applied to the molecules within the solution is not limited to that applied by laser beams. Magnetic methods or electric methods may be employed as long as they apply external force to a degree that causes differences in the amounts of time required for the reorientation of free molecules and binding molecules to become complete. In addition, it is not necessary to employ the AOD 120 as long as a structure that enables the laser beam to be emitted in two directions is utilized. For example, a configuration that utilizes a plurality of orientation controlling light sources may be adopted, and the direction that the orientation controlling light beam may be switched by switching the light source to be utilized. As another alternative, the binding molecules may be oriented by employing a linearly polarized laser beam as the orientation controlling light beam, and the directions in which the binding molecules are oriented may be switched by switching the direction in which the laser beam is linearly polarized, using a λ/2 wavelength plate or a liquid crystal phase modulating device which is controllable by electrical signals.

In addition, in the embodiments described above, the directions in which the orientation controlling light beam 117 propagates were switched between two directions perpendicular to each other, that is, that which orients the transition moments of the fluorescent molecules associated with the binding molecules to be parallel to the vibration direction of the excitation light, and that which orients the direction of the transition moments of the fluorescent molecules associated with the binding molecules to be perpendicular to the vibration direction of the excitation light. However, it is not necessary for the two directions to be perpendicular to each other. For example, in the case that a detection target substance is to be quantified, it is only necessary for one of the two directions that the orientation controlling light beam propagates in to be that which orients the direction of the transition moments of the fluorescent molecules associated with the binding molecules to be perpendicular to the vibration direction of the excitation light, that is, an orientation that does not enable the linearly polarized excitation light to excite the fluorescent molecules. If the fluorescent molecules are oriented such that the linearly polarized excitation light cannot excite the fluorescent molecules, the PD output will become noise only, because fluorescence will not be emitted. When the emission direction of the laser beam is switched to another direction, only the fluorescence emitted by the fluorescent molecules associated with the free molecules and the binding molecules for which reorientation has been completed can be received. In other words, emission of fluorescence can be temporarily reset, thereby preventing unnecessary fluorescence from being received and eliminating noise due to unnecessary fluorescence.

In this case, if the two directions that the orientation controlling light beam 117 propagates in are perpendicular, the difference in the amounts of time required for reorientation of the free molecules and the binding molecules to be completed becomes maximal, resulting in the highest S/N ratio. Meanwhile, if the angle formed by the two directions that the orientation controlling light beam 117 propagates in is 60 degrees, the amounts of time required for reorientation of the free molecules and the binding molecules to be completed will be shorter, and the amount of time required to perform measurements will also become shorter. In this manner, as the angle formed by the two directions that the orientation controlling light beam 117 propagates in decreases from 90 degrees, the amounts of time required for reorientation of the free molecules and the binding molecules to be completed will be shorter, and the amount of time required to perform measurements will also become shorter.

In addition, in the case that measurements are performed merely to ascertain whether a detection target substance is present within a solution, that is, whether binding molecules are present, it is only necessary to switch the emission direction of the orientation controlling light beam 117 into two directions having an angular difference that will cause a difference in the amounts of time required for reorientation of the binding molecules to be completed to occur. That is, it is not necessary for the two directions to include that which orients the direction of the transition moments of the fluorescent molecules associated with the binding molecules to be perpendicular to the vibration direction of the excitation light. If a difference is generated in the amounts of time required for reorientation of the binding molecules to be completed, the difference will be represented in the fluorescence data, and therefore the presence of the binding molecules can be confirmed.

Cases in which a single reagent cup is provided within the biological molecule detecting apparatus were described in the above embodiments. However, it is not necessary for a single reagent cup to be employed, and a configuration may be adopted in which a plurality of reagent cups, in which a plurality of samples are set, are provided in the biological molecule detecting apparatus. In this case, if the apparatus is configured to sequentially move the reagent cups to measurement positions and to perform measurements, a plurality of samples can be automatically measured.

Note that the above embodiments were described as cases in which antibodies labeled with fluorescent molecules were employed. However, it is not necessary to use antibodies which have already been labeled with fluorescent molecules. For example, binding of antibodies and antigens and binding of the antibodies and fluorescent molecules may be simultaneously performed within a reagent cup. In this case, a user may prepare antibodies and fluorescent molecules in separate reagent tanks, and the biological molecule detecting apparatus may dispense the antibodies, the fluorescent molecules, and a sample into a reagent cup, to cause reactions to occur when performing measurements.

In addition, the orientation controlling light source 116 and the excitation light source 118 may be configured to be removable, such that they may be replaced by those appropriate to a detection target substance and the type of fluorescent molecule.

It is desirable for the temporal intervals at which the direction of orientation control to be switched to be determined by obtaining the amount of time required for orientation of all binding molecules to be completed, based on the mass or the molecular weight of the detection target substance, the specific binding substance, and the fluorescent molecules, and the degree of orientation control exerted by the orientation control means, and designating the obtained amount of time as the length of the temporal interval. In this case, the orientation controlling light beam will not be emitted in the same direction after orientation of all of the molecules are completed, thereby reducing power consumption. In addition, measurement will not be continued extraneously, and measurement times can be shortened.

The amount of time required for orientation of all free molecules and all binding molecules to be completed may be obtained based on PD output or the output of the A/D converting section. For example, if several measurement cycles are repeated, the approximate amount of time required for the outputs to become saturated can be understood. Therefore, an arithmetic mean of the amounts of time required for the outputs to become saturated may be calculated, and the calculated amount of time may be designated as the predetermined temporal interval.

Complex mechanisms are obviated in the case that the orientation controlling light beam is employed to control the orientations of molecules compared to a case that the orientations of molecules are controlled by magnets, etc. In order to control the orientations of molecules using magnets, for example, the molecules need to be magnetic, or magnetic molecules that bind with molecules of which the orientations are to be controlled need to be prepared, and preparations for measurements become complex.

Note that in the embodiments of the present invention described above, cases were described in which plasma separated from whole blood was employed as samples. However, the sample is not limited to being whole blood, and other bodily fluids such as urine and spinal fluid may be employed as samples as long as detection target substances are dispersed within solutions thereof.

Note that the embodiments of the present invention were described as cases in which the binding molecules are oriented and the free molecules are not oriented. However, it is not necessary for the free molecules are to not be oriented. In the case that the free molecules are oriented by the orientation controlling light beam as well, the volumes and molecular weights of the free molecules and the binding molecules are different, and therefore the speeds at which they are oriented will differ. For this reason, even in the case that the emission direction of the orientation controlling light beam is switched, the amounts of time required for the switch in orientations of the molecules to be completed will differ, and the periods at which fluorescence is emitted will also differ. Therefore, if a reference signal having twice the amount of time required for the switch in orientation of the binding molecules to be completed is input to the lock in amplifier, the fluorescence components emitted by the fluorescent molecules associated with the binding molecules can be detected.

The embodiments of the present invention can perform measurements in a liquid phase, in which antigens, antibodies, and fluorescent molecules are dispersed within a solution, and therefore exhibits the advantage that preliminary processes are simple compared to solid phase measurements. Further, the antigens and the free molecules are not fixed to a solid phase, and therefore the antigens and free molecules can move freely within the solution, resulting in faster reactions than those during measurements using the solid phase.

In addition, the embodiments of the present invention do not detect changes in the degrees of fluorescent polarization due to changes in Brownian motion as in the conventional fluorescence polarization method. Therefore, even if fluorescence lifetimes are influenced by components within samples, the influence on measurements is small.

The embodiments of the present invention were described as cases in which the excitation light 119, which is linearly polarized in a single direction, is emitted onto the solution. That is, the excitation light 119 has a single polarization plane. However, it is not necessary for the excitation light 119 to be a linearly polarized light beam having a single polarization plane. In order to obtain the same advantageous effects as those obtained by the first embodiment and the second embodiment, the excitation light 119 needs only to have at least one component which is linearly polarized in a specific direction. Here, light which is linearly polarized in a specific direction is light for which changes in the relationship between the transition moments of fluorescent molecules and the vibration direction of the linearly polarized component changes the excitation efficiency of the linearly polarized component with respect to the fluorescent molecules. For example, if randomly polarized excitation light may be emitted and an analyzer may provided in front of the light receiving section such that only components of fluorescence emitted from the fluorescent molecules which are linearly polarized in a specific direction is received. Here, randomly polarized light refers to light in which the vibration direction is random, and a plurality of linearly polarized components that vibrate in various directions are present.

Figure 15A:
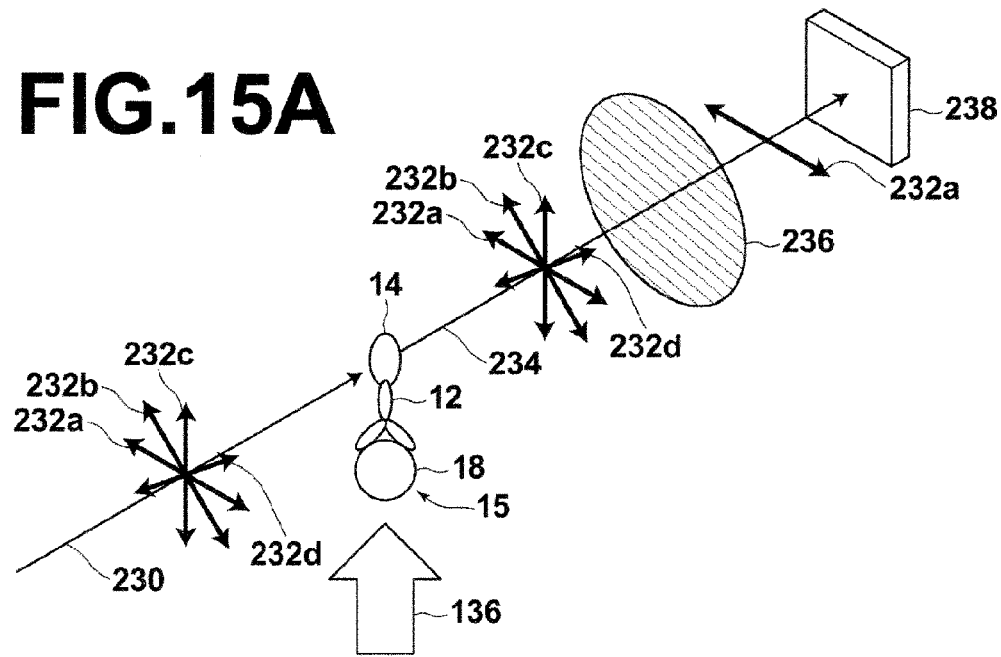
FIG. 15A is a conceptual diagram that illustrates the relationship between the transition moment of a fluorescent molecule and the vibration direction of randomly polarized excitation light in the case that an orientation controlling light beam is emitted from a first direction.
Figure 15B:
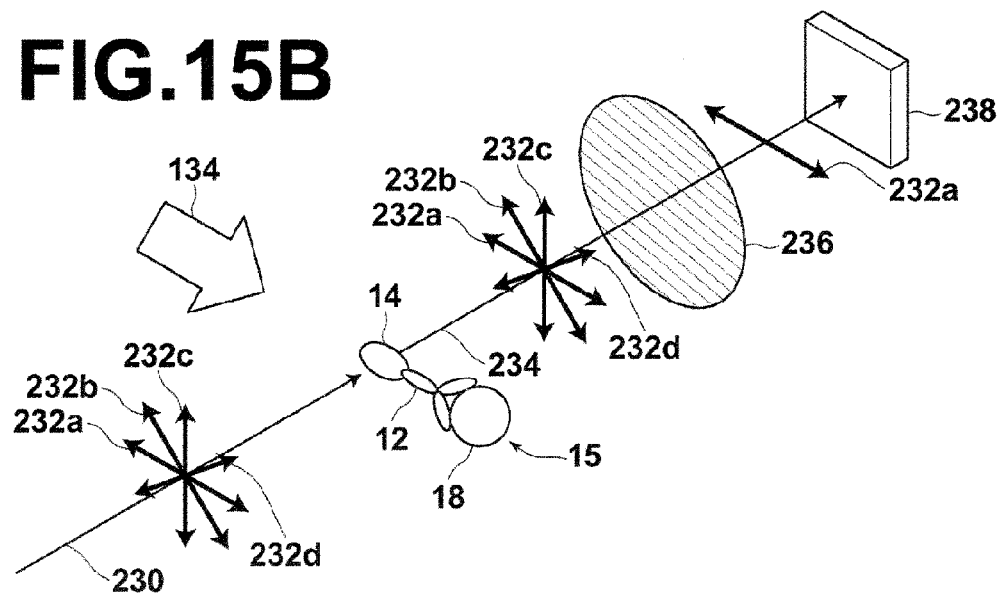
FIG. 15B is a conceptual diagram that illustrates the relationship between the transition moment of a fluorescent molecule and the vibration direction of randomly polarized excitation light in the case that an orientation controlling light beam is emitted from a second direction.

FIGS. 15A and 15B are conceptual diagrams that illustrate the relationships between the orientation direction of a fluorescent molecule 14 and the vibration directions of randomly polarized excitation light 230 in cases that an orientation controlling light beam 136 and an orientation controlling light beam 134 are emitted, respectively. The vibration directions 232a through 232d of the excitation light 230 represent the vibration directions of light within a plane perpendicular to the direction in which the excitation light 230 propagates. In FIG. 15A and FIG. 15B, the vibration directions 232a through 232d illustrate that the excitation light 230 vibrates in various directions. In actuality however, many more components having different angular directions are included in addition to the components illustrated in FIG. 15A and FIG. 15B. Generally, when fluorescent molecules which are static within a solution are excited by linearly polarized excitation light, the fluorescent molecules emit fluorescence which is polarized in the same direction as the vibration direction of the excitation light. When fluorescent molecules are excited by the randomly polarized excitation light 230, the fluorescent molecules 14 emit randomly polarized fluorescence 234.

An analyzer 236 transmits components of the randomly polarized fluorescence 234 emitted by the fluorescent molecules that vibrate in a specific direction, and cut off components that vibrate in other directions. In other words, only light that vibrates in the specific direction passes through the analyzer 236. In FIG. 15A and FIG. 15B, the component of the fluorescence 234 that vibrates in the specific direction is the only component capable of passing through the analyzer 236. Accordingly, the vibration direction of the fluorescence 234 that passes through the analyzer 236 is only the vibration direction 232a. The component that vibrates in the vibration direction 232a included in the fluorescence 234 is emitted by being excited by a component of the excitation light 230 which is linearly polarized in the vibration direction 232a. That is, only the component of the fluorescence 234 emitted by the fluorescent molecules 14 which is excited by the component of the excitation light 230 which is linearly polarized in the vibration direction 232a reaches a photodiode 238. By adopting this configuration, the same measurements as those performed by the first embodiment can be performed with respect to light that vibrates in a specific direction, even if randomly polarized light is employed as the excitation light 230. Note that the component of the fluorescence 234 that vibrates in the specific direction transmitted by the analyzer 236 is not limited to the component that vibrates in the direction described here. A component that vibrates in any direction may be transmitted by the analyzer 236 as long as differences occur in the excitation efficiency of the fluorescent molecules 14 accompanying changes in the orientation direction thereof.

In addition, FIG. 15A and FIG. 15B illustrate examples in which the amplitude of vibration is constant for all vibration directions. However, it is not necessary for the amplitude of vibration to be constant for all vibration directions. The component of the randomly polarized fluorescence 234 which is received by the photodiode 238 is only that which vibrates in the specific direction, and therefore components that vibrate in other directions are cut off.

As illustrated in FIG. 15A, when the orientation control signal is 0V, the direction of the transition moment of the fluorescent molecule 14 which is oriented by the orientation controlling light beam 136 is perpendicular to the vibration direction 232a of the component which is transmitted through the analyzer 236. In this case, the excitation efficiency of the fluorescent molecule 14 with respect to the component of the excitation light 230 that vibrates in the vibration direction 232a is minimal. Accordingly, the intensity of the component of the fluorescence 234 emitted by the fluorescent molecule 14 that passes through the analyzer 236 and reaches the photodiode 238 in this case is also minimal.

In contrast, as illustrated in FIG. 15B, when the orientation control signal is 5V, the direction of the transition moment of the fluorescent molecule 14 which is oriented by the orientation controlling light beam 134 is parallel to the vibration direction 232a of the component which is transmitted through the analyzer 236. In this case, the excitation efficiency of the fluorescent molecule 14 with respect to the component of the excitation light 230 that vibrates in the vibration direction 232a is maximal. Accordingly, the intensity of the component of the fluorescence 234 emitted by the fluorescent molecule 14 that passes through the analyzer 236 and reaches the photodiode 238 in this case is also maximal.

In the case that such a configuration is adopted as well, the orientation directions of the fluorescent molecules 14 will change when the orientation control signal is switched from 0V to 5V, and the directions of the transition moments of the fluorescent molecules 14 and the vibration direction of light which is transmitted through the analyzer 236 gradually become parallel. Accompanying this gradual approach to becoming parallel, the excitation efficiency of the fluorescent molecules 14 with respect to the component of the excitation light 230 that vibrates in the direction which is capable of being transmitted through the analyzer 236 increases. The increase in excitation efficiency results in an increase of the intensity of the component of the fluorescence 234 emitted by the fluorescent molecules 14 that vibrates in the direction which is capable of being transmitted through the analyzer 236. That is, the intensity of fluorescence detected by the photodiode 238 gradually increases in the same manner as in the first embodiment. For this reason, a graph that represents the output of the photodiode 238 over time when the orientation control signal is switched from 0V to 5V will have the same shape as the graph of FIG. 10A, even in the case that the configuration described above is adopted. That is, in this case as well, the concentration of the detection target substance can be measured by performing the same calculations as those performed in the first embodiment with respect to the graph representing the output of the photodiode 238.

Figure 16A:
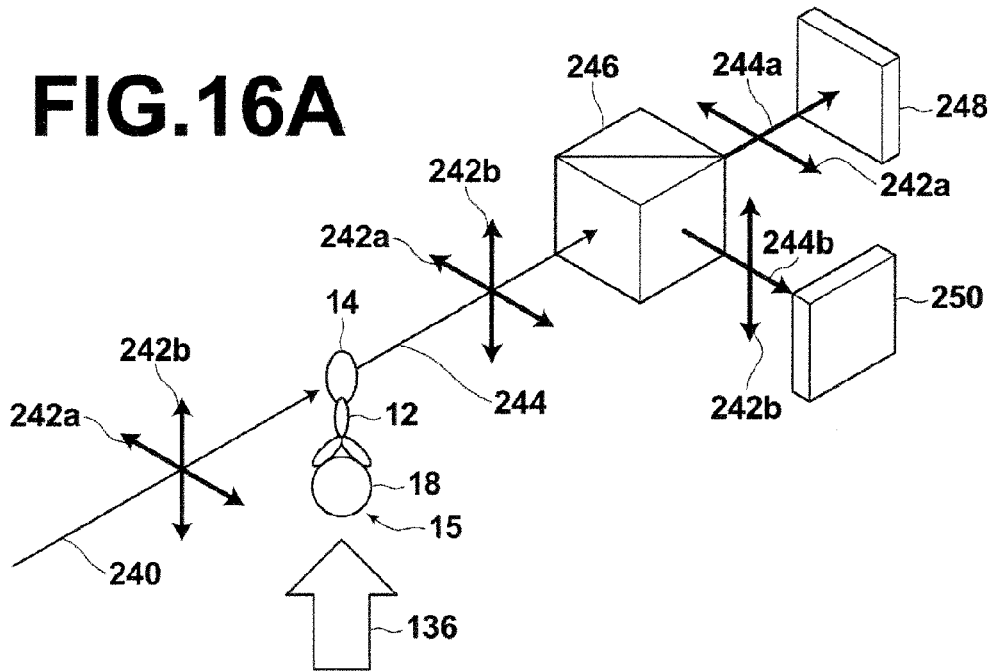
FIG. 16A is a conceptual diagram that illustrates the relationship between the transition moment of a fluorescent molecule and the vibration direction of excitation light which is linearly polarized in two directions in the case that an orientation controlling light beam is emitted from a first direction.
Figure 16B:
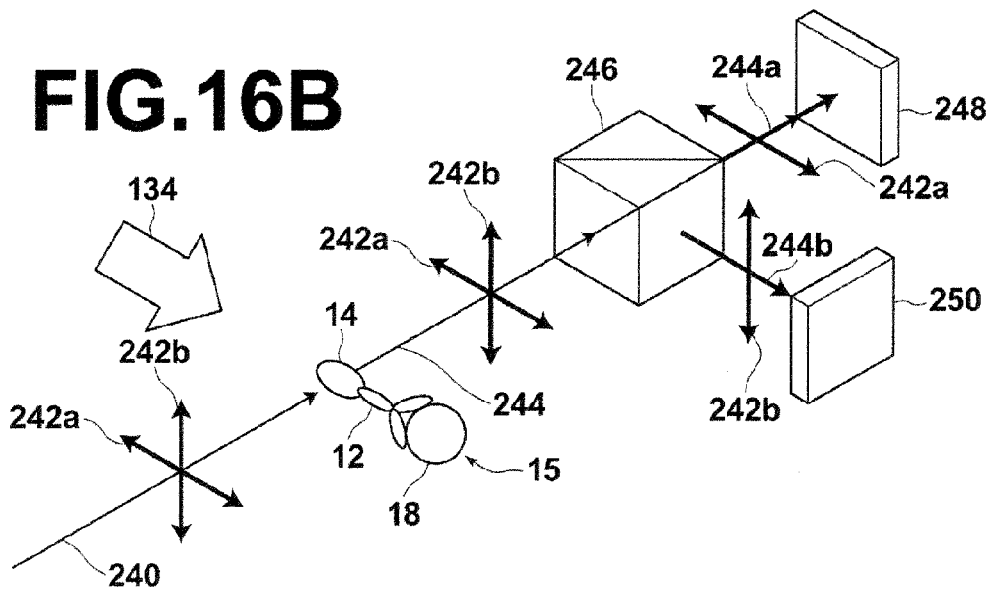
FIG. 16B is a conceptual diagram that illustrates the relationship between the transition moment of a fluorescent molecule and the vibration direction of excitation light which is linearly polarized in two directions in the case that an orientation controlling light is emitted from a second direction.

As a further alternative, excitation light 240 that consists of two components which are linearly polarized in two directions perpendicular to each other may be employed, as illustrated in the conceptual diagrams of FIG. 16A and FIG. 16B. The excitation light 240 only has two components, which are linearly polarized in vibration directions 242a and 242b within a plane perpendicular to the direction in which the excitation light 240 propagates. That is, the vibration direction 242a and the vibration direction 242b are perpendicular to each other. The fluorescent molecules 14 which are excited by the excitation light 240 emit fluorescence 244 having components that vibrate in the same vibration directions as those of the excitation light 240. That is, fluorescence 244 has two components which are linearly polarized in the vibration directions 242a and 242b.

FIG. 16A is a conceptual diagram that illustrates a case in which an orientation control signal is 0V. The orientation controlling light beam 136 is emitted when the orientation control signal is 0V. The fluorescent molecules 14 which are irradiated by the orientation controlling light beam 136 become oriented such that the transition moments thereof are the same as the vibration direction 242b. That is, the transition moments of the fluorescent molecules and the vibration direction 242b of one of the components of the excitation light 240 are parallel when the orientation control signal is 0V.

A polarizing beam splitter 246 transmits a linearly polarized component 244a of the fluorescence 244 that vibrates in the vibration direction 242a, and reflects a linearly polarized component 244b of the fluorescence 244 that vibrates in the vibration direction 242b. The linearly polarized component 244a that passes through the polarizing beam splitter 246 reaches a photodiode 248. The linearly polarized component 244b which is reflected by the polarizing beam splitter 246 reaches a photodiode 250.

FIG. 16B is a conceptual diagram that illustrates a case in which the orientation control signal is 5V. The orientation controlling light beam 134 is emitted when the orientation control signal is 5V. The fluorescent molecules 14 which are irradiated by the orientation controlling light beam 134 become oriented such that the transition moments thereof are the same as the vibration direction 242a. That is, the transition moments of the fluorescent molecules and the vibration direction 242a of the other one of the components of the excitation light 240 are parallel when the orientation control signal is 5V.

The linearly polarized component 244a of the fluorescence 244 that passes through the polarizing beam splitter 246 will be focused on. In this case, the relationship between the vibrating direction 242a of one of the components of the excitation light 240 and the direction of the transition moments of the fluorescent molecules 14 is the same as in the case of the first embodiment. Temporal changes in the output of the photodiode 248 are similar to those indicated in the graph of FIG. 10A, which was described with respect to the first embodiment. That is, the orientation directions of the binding molecules begin to change accompanying the switch in the emission direction of the orientation controlling light beam, and the output of the photodiode 248 increases. The output of the photodiode 248 becomes maximal at a point in time after reorientation of the binding molecules is complete. The orientation control signal is reset to 0V after maintaining a voltage of 5V for T seconds. When the orientation control signal is switched from 5V to 0V, the direction in which the binding molecules are oriented are switched again, and the output of the photodiode 248 decreases.

Meanwhile, the linearly polarized component 244b of the fluorescence 244 which is reflected by the polarizing beam splitter 246 will be focused on. In this case, the vibrating direction 242b of the other one of the components of the excitation light 240 and the direction of the transition moments of the fluorescent molecules 14 is parallel. Therefore, the excitation efficiency of the fluorescent molecules 14 with respect to the other component of the excitation light 240 is maximal until the emission direction of the orientation controlling light beam is switched. That is, the intensity of the linearly polarized component 244b of the fluorescence 244 is maximal until the emission direction of the orientation controlling light beam is switched, and therefore the output of the photodiode 250 that receive the linearly polarized component 244b of the fluorescence 244 reflected by the polarizing beam splitter 246 is also maximal until this time. The orientation directions of the free molecules begin to change accompanying the switch in the emission direction of the orientation controlling light beam, and the output of the photodiode 250 decreases. The output of the photodiode 250 becomes minimal after reorientation of all of the binding molecules is complete. The orientation control signal is reset to 0V after maintaining a voltage of 5V for T seconds. When the orientation control signal is switched from 5V to 0V, the direction that the binding molecules are oriented in is switched again, and the output of the photodiode 250 increases. This is because the vibration direction 242b of the other component of the excitation light 240 and the directions of the transition moments of the fluorescent molecules 14 return to being in a parallel state.

Received light data are normalized employing the output of the photodiode 248 and the output of the photodiode 250. The influence of fluctuations in the concentrations of the free molecules and the binding molecules and fluctuations in the excitation power of the optical systems can be reduced, by normalizing the outputs of the two photodiodes in this manner.

Then, the concentration of the binding molecules is calculated from the normalized received light data.

The embodiments of the present invention obtained the concentration of the binding molecules based on the saturated fluorescence intensity value. However, it is not necessary to obtain the concentration of the binding molecules in this manner. For example, lock in detection may be performed employing a high frequency in which the emission direction of the orientation controlling light beam returns to the emission direction prior to switching before the fluorescence intensity becomes saturated after switching of the emission direction of the orientation controlling light beam.

Figure 17A:
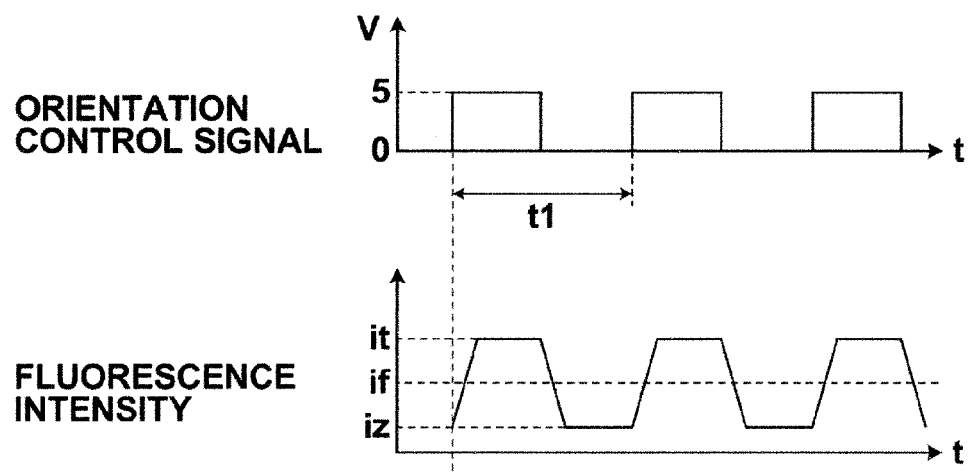
FIG. 17A is a diagram that illustrates an example in which fluorescence components synchronized with a smaller frequency of orientation control signals are detected.
Figure 17B:
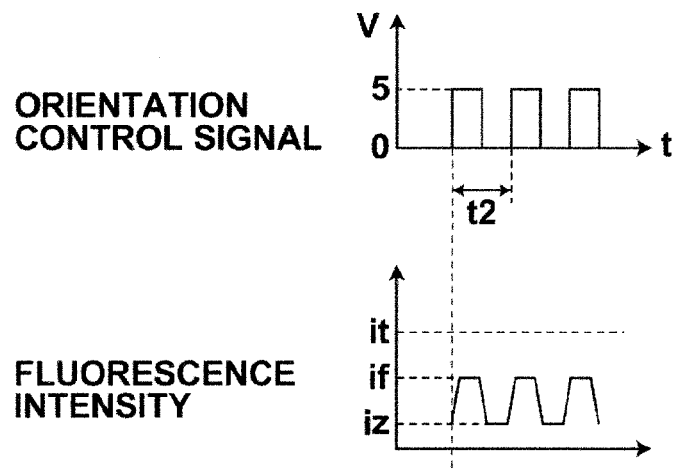
FIG. 17B is a diagram that illustrates an example in which fluorescence components synchronized with a larger frequency of orientation control signals are detected.

FIG. 17A is a graph that illustrates the output of an orientation control signal in which the period during which the orientation control signal is 5V is sufficiently long for the fluorescent intensity to become saturated. FIG. 17B is a graph that illustrates the output of an orientation control signal in which the period during which the orientation control signal is 5V is short enough for the fluorescent intensity to not become saturated. In FIG. 17A, a period t1 of the orientation control signal is sufficiently long, and the period of time during which the orientation control signal is 5V is sufficiently long. Therefore, all of the binding molecules are oriented, the fluorescence intensity becomes maximal, and the output of the lock in amplifier becomes a maximal value of i1. Meanwhile, in FIG. 17B, a period t2 of the orientation control signal is short, and the orientation control signal becomes 0V before all of the binding molecules are oriented. Therefore, the fluorescence intensity does not reach a theoretical maximum value, and the output of the lock in amplifier is i2.

In the embodiments of the present invention, the number of orientation controlling light sources is not limited to one for each emission direction. A plurality of orientation controlling light sources may be provided, and a plurality of orientation controlling light beans may be emitted in the same direction.

In optical systems that control the directions of the transition moments of fluorescent molecules by changing the direction in which an orientation controlling light beam is emitted, a plurality of optical systems that simultaneously emit orientation controlling light beams toward a plurality of points from a certain direction may be provided to broaden the irradiation range of the orientation controlling light beams, in order to avoid a problem that the range that the orientation controlling light beam can irradiated will become small in cases that the orientation controlling light beam is focused into a narrow range. The plurality of optical systems may have a plurality of optical paths at least at a stage prior to the laser beam entering the reagent cup. For example, if three optical systems that also include light sources are provided, external force imparting light beams are emitted from all three external force imparting light sources, and the external force imparting light beams can irradiate three points of the reagent cup from a certain direction. As another example, a single external force imparting light beam may be branched by employing a two dimensional laser array, a microlens array, etc, and the external force imparting light beams can be emitted onto a plurality of points corresponding to the number of branches, even if only a single light source is provided. In such a case, the orientation controlling light beam can be simultaneously emitted onto a plurality of points, and the transition moments of the fluorescent molecules can be rotated at a plurality of locations.

The embodiments of the present invention were described as cases in which the directions of the transition moments of the fluorescent molecules are controlled by switching the direction in which the laser beam is emitted. However, the method for controlling the directions of the transition moments of the fluorescent molecules is not limited to this configuration. For example, the directions of the transition moments of the fluorescent molecules may be controlled by controlling the vibration direction of a linearly polarized laser beam, utilizing the phenomenon that the transition moments of fluorescent molecules track the vibration direction of linearly polarized light.

An example of a method for controlling the directions of the transition moments of the fluorescent molecules by controlling the vibration direction of a linearly polarized laser beam will be described. A laser beam which is linearly polarized in a single direction is employed, and the polarization axis of the laser beam is rotated to control the orientations of the binding molecules, thereby controlling the directions of the transition moments of the fluorescent molecules. The polarization axis of the linearly polarized laser beam may be controlled by employing a $\lambda/2$ wavelength plate. $\lambda/2$ wavelength plates are phase plates that function to cause optical path differences between two perpendicular components of light to half the wavelength thereof, and are employed to rotate the polarization axes of light. Light which is linearly polarized in a direction parallel to the direction of the optical axis of a $\lambda/2$ wavelength plate passes therethrough as is, whereas light which is linearly polarized in a direction that forms a 45 degree angle with the direction of the optical axis of a $\lambda/2$ wavelength plate is transmitted in a state in which the polarization axis thereof is rotated 90 degrees. That is, switching between a case in which a laser beam passes through the $\lambda/2$ wavelength plate as is and a case in which a laser beam is transmitted in a state in which the polarization axis thereof is rotated 90 degrees is enabled, by switching the angle of the $\lambda/2$ wavelength plate with respect to the linearly polarized laser beam. That is, the binding molecules can be oriented in two directions by rotating the polarization axis of the linearly polarized laser beam employing the $\lambda/2$ wavelength plate.

Figure 18A:
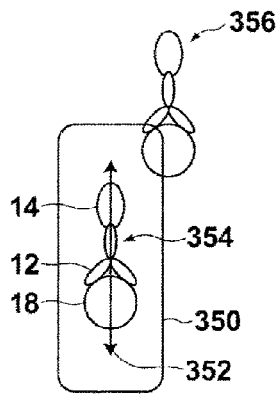
FIG. 18A is a first conceptual diagram for explaining changes in the orientation of a binding molecule accompanying changes in the polarization axis of an orientation controlling light beam.

In the case that the directions of the transition moments of the fluorescent molecules are controlled by controlling the vibration direction of the linearly polarized orientation controlling light beam, the orientation controlling light beam may be of any cross sectional shape within a plane perpendicular to the propagation direction thereof. For example, a case will be considered in which a linearly polarized orientation controlling light beam 350 having a polarization axis 352 is emitted, as illustrated in FIG. 18A. In this case, the laser beam 250 has a substantially rectangular cross sectional shape in a direction perpendicular to the propagation direction thereof. The motions of a binding molecule 354 positioned at the center of the orientation controlling light beam 350 and a binding molecule 356 positioned at the peripheral portion of the orientation controlling light beam 350 will be considered.

Figure 18B:
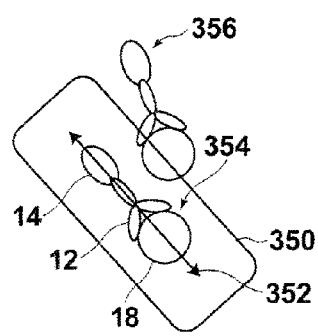
FIG. 18B is a second conceptual diagram for explaining changes in the orientation of a binding molecule accompanying changes in the polarization axis of an orientation controlling light beam.
Figure 18C:
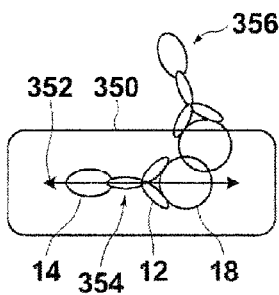
FIG. 18C is a third conceptual diagram for explaining changes in the orientation of a binding molecule accompanying changes in the polarization axis of an orientation controlling light beam.

As illustrated in FIG. 18B, the polarization axis 352 rotates when the orientation controlling light beam 350 is rotated. The binding molecule 354 which is positioned on the rotational axis (the center of rotation of the polarization axis 352) immediately tracks the rotation of the polarization axis 352, and rotates. Meanwhile, the binding molecule 356 positioned at the peripheral portion of the orientation controlling light beam 350 cannot track the rotation of the polarization axis 352 immediately, and becomes separated therefrom. After a period of time, the binding molecule 356 is also drawn into the orientation controlling light beam 350, and initiates rotation that tracks the rotation of the polarization axis 352. In the case that the polarization axis 352 of the orientation controlling light beam 350 is rotated 90 degrees from the polarization axis 352 of FIG. 18A as illustrated in FIG. 18C, the reorientation of the binding molecule 354 is completed simultaneously with the completion of rotation of the polarization axis 352. Meanwhile, because the binding molecule 356 cannot track the rotation of the polarization axis 352 immediately, reorientation of the binding molecule 356 is completed after a period of time following completion of rotation of the polarization axis 352. That is, the movement of the binding molecule 354 positioned on the rotational axis is rotation which is synchronized with the rotation of the polarization axis 352 of the orientation controlling light beam 350. However, the movement of the binding molecule 356 positioned at the peripheral portion of the orientation controlling light beam 350 is revolution about the rotational axis which is not synchronized with the rotation of the polarization axis 352 of the orientation controlling light beam 350.

Figure 19:
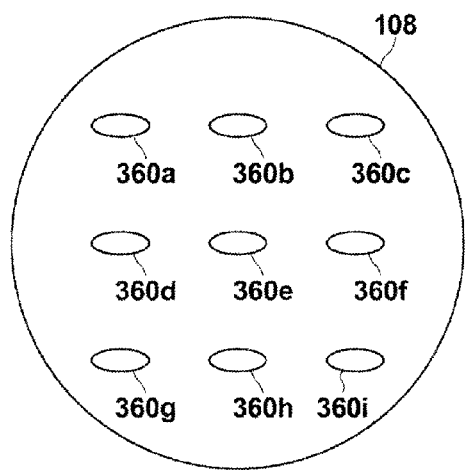
FIG. 19 is a conceptual diagram that illustrates a case in which linearly polarized laser beams are emitted onto a plurality of points in a reagent cup from the bottom surface thereof.

There are cases in which the presence of binding molecules that cannot track the rotation of the polarization axis 352 of the orientation controlling light beam 350 will influence measurements. In order to reduce such influence, it is preferable for the orientation controlling light beam to simultaneously enter a plurality of points from a predetermined direction. For example, as illustrated in FIG. 19 (a plan view of the reagent cup 108) a configuration may be adopted, in which nine orientation controlling light beams corresponding to nine points 360a through 360i enter the reagent cup 108. By adopting such a configuration, the number of binding molecules which are positioned at the center of the polarization axes of the orientation controlling light beams will increase, thereby reducing the aforementioned influence on measurements. Note that although an example in which orientation controlling light beams enter nine points is described here, the number of points that the orientation controlling light beams enter is not limited to nine, and may be greater or less than nine. It is desirable for orientation controlling light beams to enter a greater number of points the narrower that they are focused. Thereby, the binding molecules can be caused to rotate in synchrony with the rotation of the orientation controlling light beams. As a result, sudden variations in fluorescent intensity can be reduced, and the coefficient of variation, which is an index that represents relative spreading, can be improved.

Figure 20:
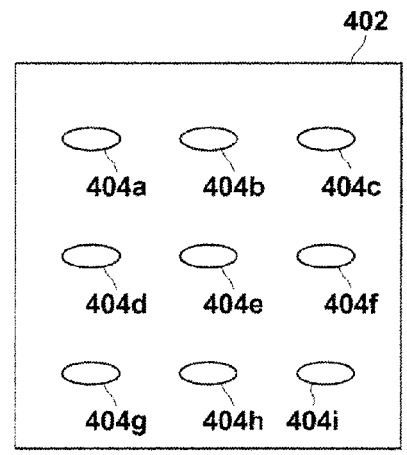
FIG. 20 is a conceptual diagram that illustrates the structure of an orientation controlling light source for causing linearly polarized orientation controlling light beams to be emitted onto a plurality of points from a predetermined direction.

The structure of an orientation controlling light source 402 that causes laser beams to simultaneous enter a plurality of points from a predetermined direction is illustrated in FIG. 20. The orientation controlling light source 402 is a 3·3 two dimensional laser array. Nine light emitting points 404a through 404i of the orientation controlling light source 402 emit light. The light emitting points have heights of 1 μm and widths of 100 μm. The distances among the light emitting points are approximately 100 μm.

Figure 21:
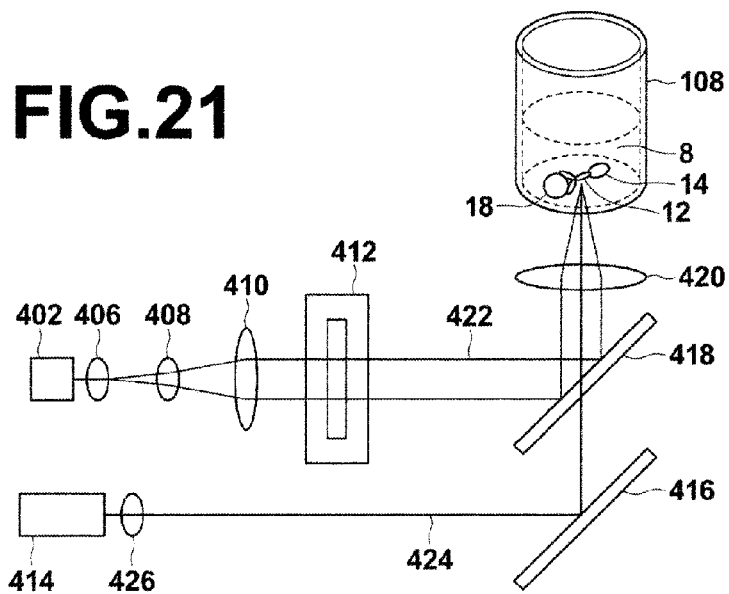
FIG. 21 is a conceptual diagram that illustrates an example of the structure of an optical system for causing linearly polarized orientation controlling light beams to be emitted onto a plurality of points from a predetermined direction.

An example of an optical system that employs the orientation controlling light source 402 of FIG. 20 is illustrated in FIG. 21. Note that structural elements other than the optical systems for laser beams and excitation light are omitted in FIG. 21.

Linearly polarized orientation controlling light beams 422 output from the orientation controlling light source 402 pass through a collimating lens 406 and become collimated light beams at a focal point. The orientation controlling light beams 422 which have passed through the collimating lens 406 pass through beam expanders 408 and 410, then enter a $\lambda/2$ wavelength plate 412. The orientation controlling light beams 422 which have passed through the beam expanders 408 and 410 are spread to become a collimated light beam having a specific magnification ratio. The $\lambda/2$ wavelength plate is on a rotatable stage, and is configured to be rotatable. This configuration enables the vibration direction of the orientation controlling light beams 422 to be rotated. The orientation controlling light beams 422 which have passed through the $\lambda/2$ wavelength plate are reflected by a dichroic mirror 418, focused by a lens 420, enter the reagent cup 108 through the bottom surface thereof, and propagate upward.

Excitation light 424 output from a light source 414 passes through a lens 426 and is reflected by a dichroic mirror 416. The excitation light 424 which has been reflected by the dichroic mirror 416 passes through a dichroic mirror 418, is focused by a lens 420, enters the reagent cup 108 through the bottom surface thereof, and propagates upward.

If the focal distance of the collimating lens 406 is set to be 3.1 mm, and the focal distance of the lens 420 is set to be 4 mm in the optical system illustrated in FIG. 21, the magnification ratio will be 1.29×. Therefore, the sizes of the orientation controlling light beams 422 are approximately 1.3 μm·130 μm with pitches of approximately 129 μm at the bottom surface of the reagent cup 108.

Another example of an optical system that causes laser beams to simultaneously enter a plurality of points from a predetermined direction will be described with reference to FIG. 22. Note that structural elements other than the optical systems for orientation controlling light beams and excitation light are omitted in FIG. 22. In addition, structural elements which are the same as those illustrated in FIG. 21 are denoted by the same reference numerals, and detailed descriptions thereof will be omitted.

Figure 22:
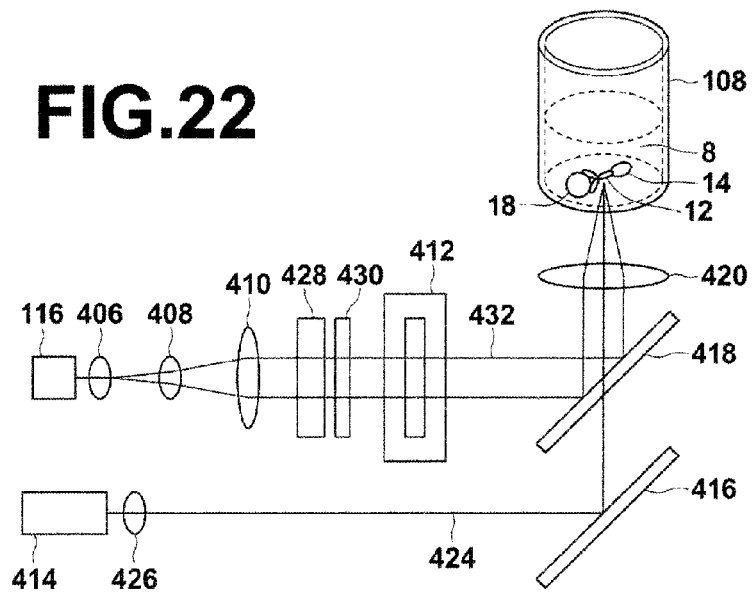
FIG. 22 is a conceptual diagram that illustrates another example of the structure of an optical system for causing linearly polarized orientation controlling light beams to be emitted onto a plurality of points from a predetermined direction.
Figure 23:
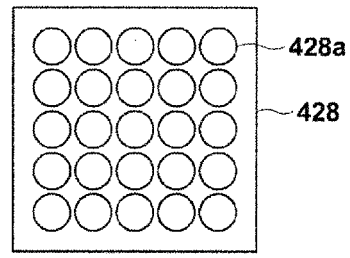
FIG. 23 is a conceptual diagram that illustrates a microlens array.

In the optical system illustrated in FIG. 22, the orientation controlling light source 116 is the same as that of the first embodiment. An orientation controlling light beam 432 passes through the collimating lens 406, the beam expanders 408 and 410, and enters a microlens array 428. As illustrated in FIG. 23, the microlens array 428 has a plurality of microlenses 428a arrayed in a lattice shape. The orientation controlling light beam 432 which passes through the microlens array 428 becomes a plurality of light beams which have different focal points, as light emitted by a plurality of light sources. The orientation controlling light beam 432 is focused by a pinhole array 430, reflected by the dichroic mirror 418, focused by the lens 420, enters the reagent cup 108 through the bottom surface thereof, and propagates upward. Orientation controlling light beams can be caused to simultaneously enter a plurality of points from a predetermined direction by employing a microlens array in this manner as well.

Figure 24:
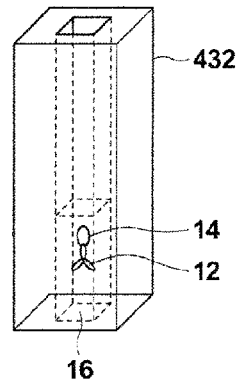
FIG. 24 is a conceptual diagram that illustrates an example of the shape of a reagent cup.

In addition, the reagent cup was of a cylindrical shape in the embodiments described above. However, it is not necessary for the shape of the reagent cup to be cylindrical. For example, a reagent cup 432 shaped as a rectangular column and having a rectangular columnar solution portion therein may be employed, as illustrated in FIG. 24. The reagent cup 432 having the rectangular columnar solution portion is particularly suited in cases that pressure applied by the orientation controlling light beam in the propagation direction thereof is utilized to press the binding molecules against the surface of an inner wall of the reagent cup 432. This is a phenomenon that occurs in cases that the masses of the binding molecules are light, caused by the binding molecules moving through the solution under the pressure applied by the orientation controlling light beam. In this case, if the solution holding portion is a rectangular column, the free molecules and the binding molecules are oriented while being pressed against the interface between the solution and the reagent cup 432. In the case that the interface is a flat surface and the pressure applied by the orientation controlling light beam operates in a direction perpendicular to the interface, the binding molecules will not move outside the irradiation range of the orientation controlling light beam by moving in directions parallel to the interface.

Figure 25:
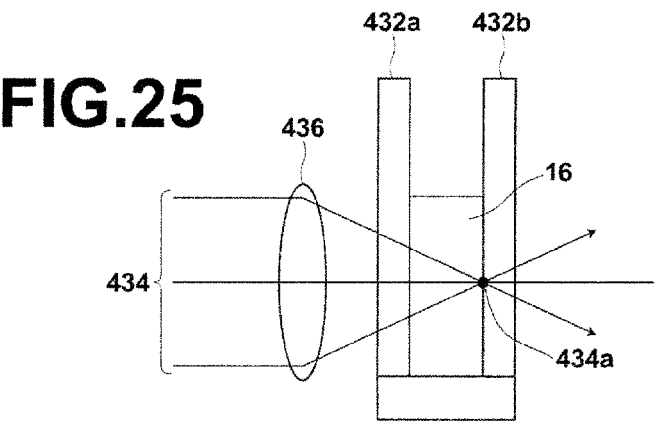
FIG. 25 is a conceptual diagram that illustrates an example of the positional relationship between the focal point of a focused orientation controlling light beam and a reagent cup.

In addition, in the case that the binding molecules are pressed against the surface of the inner wall of the reagent cup 432, the molecules can be more easily oriented by setting the position of the focal point of the orientation controlling light beam. FIG. 25 is a diagram that illustrates the positional relationship between the focal point of a focused orientation controlling light beam and a reagent cup. An orientation controlling light beam 434 enters a lens 436 and is focused at a focal point 434a at the interface between the plasma 16 and a side wall 432b (the inner surface of the side wall 432b). The intensity of the orientation controlling light beam 434 is greatest at the position of the focal point 434a, and therefore the binding molecules can be pressed with a great amount of pressure. Accordingly, if the orientation controlling light beam 434 is emitted in the manner illustrated in FIG. 25, the binding molecules can be more efficiently oriented while pressing the binding molecules against the inner surface of the side wall 432b. In this case as well, the orientation directions of the binding molecules can be changed at the position of the focal point 434a by rotating the vibration direction of the linearly polarized orientation controlling light beam 434.

Note that it is not necessary for the solution holding portion to be shaped as a rectangular column, and the solution holding portion needs only to have at least one flat surface. If an orientation controlling light beam is emitted such that it is focused at a focal point on the flat surface, the binding molecules will not move outside the irradiation range of the orientation controlling light beam by moving in directions parallel to the flat surface, and will be oriented while being pressed against the flat surface.

FIELD OF INDUSTRIAL APPLICABILITY

The biological molecule detecting apparatus and the biological molecule detecting method of the present invention may be utilized in apparatuses that detect or quantify detection target substances by utilizing interactions between the detection target substances and substances that specifically bind to the detection target substances.

What is claimed is:

1. A biological molecule detecting apparatus that detects fluorescence emitted by a first complex and a second complex within a solution, the first complex being formed by a substance that specifically binds with a detection target substance bound to a fluorescent molecule, and the second complex being formed by the first complex bound to the detection target substance, to detect or quantify the detection target substance, comprising:

a light source that emits excitation light having a light component which is linearly polarized in a specific direction that excites the fluorescent molecules;

a light receiving section that detects the fluorescence emitted by the fluorescent molecules;

orientation control means for periodically switching the orientation of the second complex within the solution;

synchronous component extracting means for extracting components of the fluorescence detected by the light receiving section which are synchronized with the period at which the second complex is oriented; and a calculating section that detects or quantifies the detection target substance based on the component extracted by the synchronous component extracting means.

2. A biological molecule detecting apparatus as defined in claim 1, wherein:

the orientation control means switches the orientation of the second complex between an orientation in a first direction in which the direction of the transition moments of the fluorescent molecules and the vibration direction of the linearly polarized component of the excitation light are parallel, and an orientation in a second direction in which the direction of the transition moments of the fluorescent molecules and the vibration direction are perpendicular.

3. A biological molecule detecting apparatus as defined in claim 2, wherein:

the period at which the orientation of the second complex is switched is determined by one of the molecular weight and the volume of the detection target substance, one of the molecular weight and the volume of the substance that specifically binds to the detection target substance, one of the molecular weight and the volume of the fluorescent molecule, and the intensity of orientation control exerted by the orientation control means.

4. A biological molecule detecting apparatus as defined in claim 3, wherein:

the orientation control means is equipped with an orientation controlling light source that emits light having a wavelength different from that of the excitation light, that controls the orientation of the second complex.

5. A biological molecule detecting apparatus as defined in claim 4, wherein:

the orientation controlling light source emits the light having a wavelength different from that of the excitation light onto the solution from a plurality of positions.

6. A biological molecule detecting apparatus as defined in claim 2, wherein:

the orientation control means is equipped with an orientation controlling light source that emits light having a wavelength different from that of the excitation light, that controls the orientation of the second complex.

7. A biological molecule detecting apparatus as defined in claim 6, wherein:

the orientation controlling light source emits the light having a wavelength different from that of the excitation light onto the solution from a plurality of positions.

8. A biological molecule detecting apparatus as defined in claim 1, wherein:

the period at which the orientation of the second complex is switched is determined by one of the molecular weight and the volume of the detection target substance, one of the molecular weight and the volume of the substance that specifically binds to the detection target substance, one of the molecular weight and the volume of the fluorescent molecule, and the intensity of orientation control exerted by the orientation control means.

9. A biological molecule detecting apparatus as defined in claim 8, wherein:

the orientation control means is equipped with an orientation controlling light source that emits light having a wavelength different from that of the excitation light, that controls the orientation of the second complex.

10. A biological molecule detecting apparatus as defined in claim 9, wherein:

the orientation controlling light source emits the light having a wavelength different from that of the excitation light onto the solution from a plurality of positions.

11. A biological molecule detecting apparatus as defined in claim 1, wherein:

the orientation control means is equipped with an orientation controlling light source that emits light having a wavelength different from that of the excitation light, that controls the orientation of the second complex.

12. A biological molecule detecting apparatus as defined in claim 11, wherein:

the orientation controlling light source emits the light having a wavelength different from that of the excitation light onto the solution from a plurality of positions.

13. A biological molecule detecting apparatus as defined in claim 12, further comprising:

a solution holding portion for holding the solution, having a flat surface at least at a portion thereof.

14. A biological molecule detecting apparatus as defined in claim 13, wherein:

the orientation controlling light source emits the light having a wavelength different from that of the excitation light in a direction that passes through the solution and exits the flat surface of the solution holding portion such that the light is focused at an interface between the solution and the flat surface.

15. A biological molecule detecting apparatus as defined in claim 11, further comprising:

a solution holding portion for holding the solution, having a flat surface at least at a portion thereof.

16. A biological molecule detecting apparatus as defined in claim 15, wherein:

the orientation controlling light source emits the light having a wavelength different from that of the excitation light in a direction that passes through the solution and exits the flat surface of the solution holding portion such that the light is focused at an interface between the solution and the flat surface.

17. A biological molecule detecting apparatus as defined in claim 1, wherein:

the light receiving section is equipped with spectral means for spectrally separating light.

18. A biological molecule detecting apparatus as defined in claim 17, wherein:

the spectral means is a plurality of filters having different properties; and the light receiving section switches a filter to be employed from among the plurality of filters according to the emission wavelength of the fluorescence.

19. A biological molecule detecting method for detecting fluorescence emitted by a first complex and a second complex within a solution, the first complex being formed by a substance that specifically binds with a detection target substance bound to a fluorescent molecule, and the second complex being formed by the first complex bound to the detection target substance, to detect or quantify the detection target substance, comprising:

a step of emitting excitation light having a light component which is linearly polarized in a specific direction that excites the fluorescent molecules;

a step of periodically switching the orientation of the second complex within the solution;

a step of detecting the fluorescence emitted by the fluorescent molecules;

a step of extracting components of the detected fluorescence which are synchronized with the period at which the second complex is oriented; and a step of detecting or quantifying the detection target substance based on the extracted component.

* * * * *

UNITED STATES PATENT AND TRADEMARK OFFICE
CERTIFICATE OF CORRECTION

| | | Page 1 of 1 |
|---|---|---|
| PATENT NO. | : 8,680,486 B2 | |
| APPLICATION NO. | : 13/854640 | |
| DATED | : March 25, 2014 | |
| INVENTOR(S) | : Toshihito Kimura | |

It is certified that error appears in the above-identified patent and that said Letters Patent is hereby corrected as shown below:

On the Title page:

Insert --(60) Continuation of application No. PCT/JP/2011/005487, filed on September 29, 2011.--

Signed and Sealed this
Twentieth Day of January, 2015

Michelle K. Lee
*Deputy Director of the United States Patent and Trademark Office*